United States Patent [19]

Johnson et al.

[11] Patent Number: 5,057,302

[45] Date of Patent: Oct. 15, 1991

[54] BIFUNCTIONAL CHELATING AGENTS

[75] Inventors: David K. Johnson, Vernon Hills; Steven J. Kline, Grayslake, both of Ill.

[73] Assignee: Abbott Laboratories, North Chicago, Ill.

[21] Appl. No.: 136,180

[22] Filed: Jan. 4, 1988

Related U.S. Application Data

[63] Continuation-in-part of Ser. No. 14,517, Feb. 13, 1987, abandoned.

[51] Int. Cl.$^5$ .................. A61K 49/00; A61K 39/44; C07K 17/00; C12N 11/00; C12Q 1/00; C12Q 1/25

[52] U.S. Cl. ......................................... 424/1.1; 424/9; 424/85.9; 424/93; 424/94.3; 530/345; 530/388; 530/390; 530/391; 530/395; 530/408; 530/409; 530/410; 435/7.92; 435/174; 435/177; 558/17; 514/6; 514/32; 514/42; 514/54; 514/171; 536/1.1; 536/17.6; 536/22; 534/10; 534/15; 436/501; 436/504

[58] Field of Search .................. 424/1.1, 9, 85.91, 93, 424/94.3; 530/345, 408, 409, 390, 391, 395, 388, 410; 558/17; 534/10, 15; 514/6, 171, 32, 42, 54; 536/17.6, 22, 1.1; 435/174, 177, 7

[56] References Cited

U.S. PATENT DOCUMENTS

| | | | |
|---|---|---|---|
| 3,994,966 | 11/1976 | Sundberg et al. | 562/437 |
| 4,454,106 | 6/1984 | Gansow et al. | 424/1.1 |
| 4,647,447 | 3/1987 | Gries et al. | 424/9 |
| 4,678,667 | 7/1987 | Meares et al. | 424/85.91 |
| 4,826,673 | 5/1989 | Dean et al. | 424/9 |
| 4,831,175 | 5/1989 | Gansow et al. | 558/17 |
| 4,885,363 | 12/1989 | Tweedle et al. | 540/465 |

FOREIGN PATENT DOCUMENTS

| | | | |
|---|---|---|---|
| 0088695 | 9/1983 | European Pat. Off. | |
| 0097373 | 1/1984 | European Pat. Off. | |
| 0130934 | 1/1985 | European Pat. Off. | 424/9 |
| 0173629 | 3/1986 | European Pat. Off. | 424/85.91 |
| 0174853 | 3/1986 | European Pat. Off. | |

OTHER PUBLICATIONS

Franz et al. (1987) Nucl. Med. Biol. 14(5):479–484.
Moi et al. (1987) Inorganic Chem. 26(21):3458-63.
Westerberg et al. (1989) J. Med. Chem. 32:236-3.
Altman et al., J. Chem. Soc. Perkin Trans. I., 365-368 (1983).
Altman et al., J. Chem. Soc. Perkin Trans. I., 59 (1984).
Borch et al., J. Amer. Chem. Soc., 93, 2897 (1971).
Brechbiel et al., Inorg. Chem., 25, 2772-81 (1986).
Buchsbaum et al., Int. J. Nucl. Med. Biol., vol. 12, No. 2, pp. 79-82, 1985.
Burnett et al., Biochem. Biophys. Res. Comm., 96, No. 1, 157-62 (1980).
Colcher et al., Cancer Res., 44, 5744 (1984).
DeRiemer et al., J. Med. Chem., 22, No. 9, 1019-23 (1979).
Goldenberg et al., N. Eng. J. Med., 298, 1384-88 (1978).
Goodwin et al., J. Nucl. Med., 22, No. 9, 787-92 (1981).
Green et al., Int. J. Nucl. Med. Biol., 12, No. 5, 381-86 (1985).
Haner et al., Arch. Biochem. Biophys., 231, No. 2, 477-86 (1984).
Hnatowich et al., J. Immunol. Meth., 65, 147 (1983).
Hwang and Wase, Biochim. Biophys. Acta, 512, 54-71 (1978).
Keenan et al., J. Nucl. Med., 25, 1197 (1984).
Kroll et al., Nature, 180, 919-20 (1957).
Laemmli et al., Nature, 227, 680 (1970).
Meares et al., J. Protein Chem., 3, No. 2, 215-228 (1984).
Meares et al., Anal. Biochem., 142, 68-78 (1984).
Moi et al., Anal. Biochem., 148, 249-253 (1985).

(List continued on next page.)

Primary Examiner—Jeffrey E. Russel
Assistant Examiner—Kay Kim

[57] ABSTRACT

The present invention provides bifunctional chelating agents comprising a unique substrate reactive moiety incorporated into a carboxymethyl arm of a polyaminopolycarboxylate chelating framework capable of forming stable complexes with metal ions.

29 Claims, 1 Drawing Sheet

OTHER PUBLICATIONS

Morrison et al., Proc. Nat. Acad. Sci. U.S.A., 81, 6851–55 (1984).
Order et al., Int. J. Radiation Oncology Biol. Phys., 12, 277–81 (1986).
Paik et al., J. Nucl. Med., 24, No. 12, 1158 (1983).
Parham et al., J. Immunology, 131, 2895 (1983).
Porath and Olin, Biochemistry, 22, 1621–30 (1983).
Rosenberg et al., Biochemistry, 11, No. 19, 3623–28 (1972).
Schlom et al., Int. J. Cancer, 29, 539 (1982).
Schultz and Dervan, J. Amer. Chem. Soc., 105, 7748–50 (1983).
Sundberg et al., J. Med. Chem., 17, No. 12, 1304 (1974).
Takeshita and Maeda, Yukagaku, 19(10):984–93 (50–59) (1970).
Taliaferro et al., Inorg. Chem., 23, 1188–92 (1984).
Zalcberg and McKenzie, J. Clin. Oncology, vol. 3; pp. 876–881 (1985).
Zittle, Advan. Enzym., 12, 493, 513, 514, 520–22 (1951).

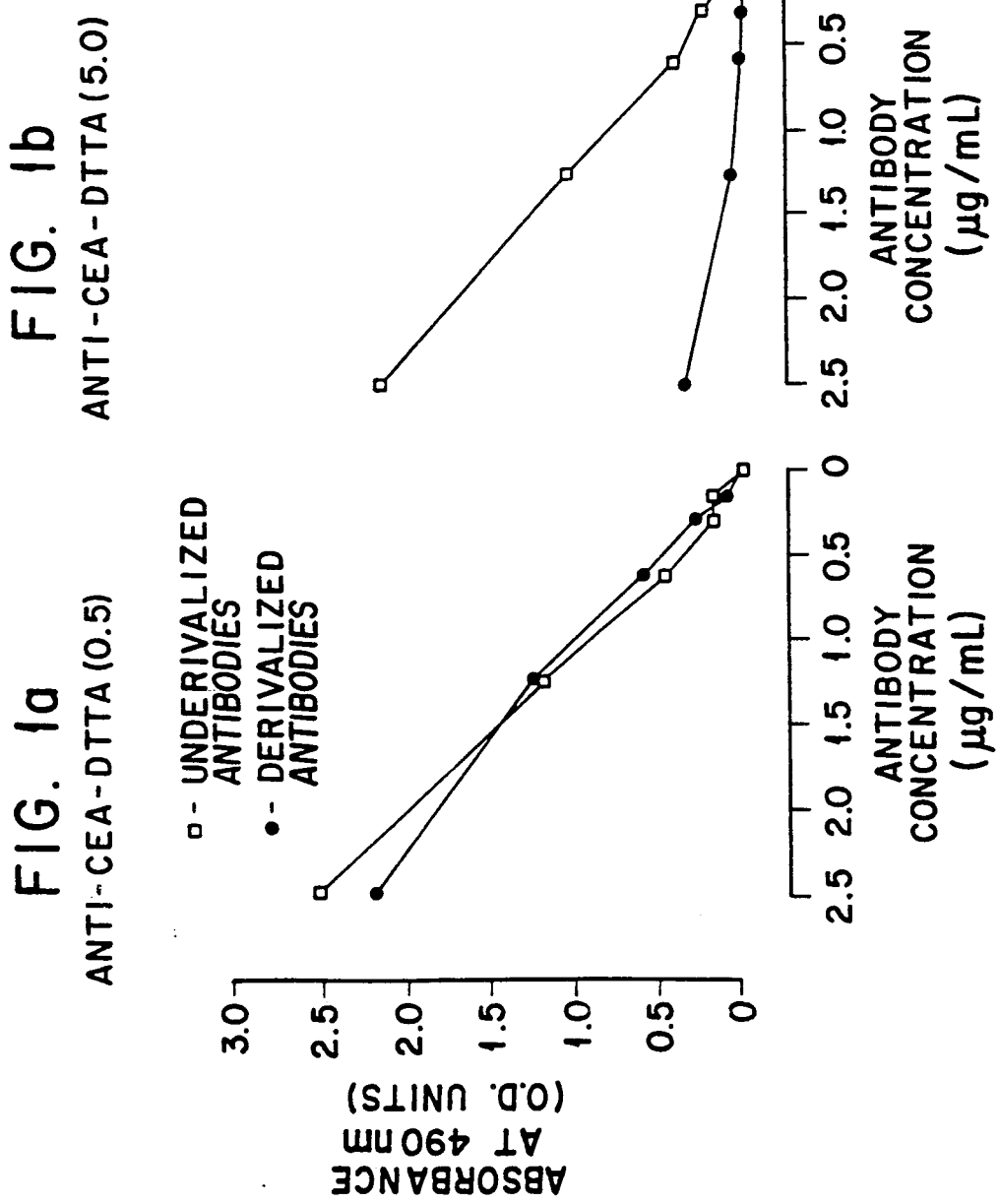

BIFUNCTIONAL CHELATING AGENTS

This is a continuation-in-part application of Ser. No. 014,517, filed Feb. 13, 1987, now abandoned.

BACKGROUND

The present invention relates generally to chelating agents for the binding of metal ions to biologically active molecules, both naturally occurring and synthetic. Specifically, it relates to bifunctional chelating agents comprising an array of metal-binding groups plus a single additional moiety (hereafter a "substrate reactive" group) which is reactive with one or more functionalities present on the molecule to be labelled with a metal ion (hereafter the "substrate"). According to one embodiment, the invention relates to antibody conjugates and antibody-metal ion conjugates comprising the bifunctional chelating agents and to the use of such antibody-metal ion conjugates for in vivo diagnostic imaging methods utilizing radiation emitting and radiation absorbing metal ions. The invention additionally relates to therapeutic methods involving the use of such antibody-metal ion conjugates whic emit cytotoxic radiation.

Of interest to the present invention are disclosures showing the use of protein/metal ion conjugates for diagnostic and therapeutic purposes. Gansow, et al., U.S. Pat. No. 4,454,106 discloses the use of monoclonal antibody/metal ion conjugates for in vivo and in vitro radioimaging diagnostic methods. Goldenberg, et al., N. Eng. J. Med., 298 1384-88 (1978) discloses diagnostic imaging experiments wherein antibodies to the known tumor associated antigen carcinoembryonic antigen (CEA) are labelled with iodine$^{131}$ and injected into patients with cancer. After 48 hours, the patients are scanned with a gamma scintillation camera and tumors are localized by the gamma emission pattern.

Other workers disclose the therapeutic use of antibody/metal ion conjugates for delivery of cytotoxic radioisotopes to tumor deposits in vivo. Order, et al., Int. J. Radiation Oncology Biol. Phys., 12, 277-81 (1986) describes treatment of hepatocellular cancer with antiferritin polyclonal antibodies to which yttrium$^{90}$ has been chelated. Duchsbaum, et al., Int. J. Radiation Oncology Biol. Phys., 12, 79-82 (1985) discloses radiolabelling of monoclonal antibodies to CEA with yttrium$^{88}$ and suggests the possibility of localization and treatment of colorectal cancers therewith. Nicolotti, EPO Application No. 174,853 published Mar. 19, 1986, discloses conjugates comprising metal ions and antibody fragments. According to that disclosure, monoclonal antibodies of subclass IgG are enzymatically treated to remove the Fc fragment and reductively cleave the disulfide bond linking the antibody heavy chains. The Fab' fragment is then linked to a chelating agent bound to a radionuclide metal ion for in vivo diagnostic or therapeutic use.

Antibody/metal ion conjugates may be formed through the use of bifunctional chelating agents comprising an array of metal-binding groups plus a moiety capable of covalent binding to a protein substrate. Early work with bifunctional chelating agents involved the compound diethylenetriaminepentaacetic acid (DTPA) and its derivatives. This compound comprises a backbone of three nitrogen atoms linked by two ethylene chains. Extending from the nitrogen atoms on the backbone are five carboxymethyl moieties. Methods have been described whereby one of the carboxymethyl groups may be reacted to form an amide bond with an amino acid residue present on an antibody or other protein molecule. The other four carboxymethyl moieties, together with the three nitrogen atoms, then remain available for metal binding. Unfortunately, because there is no intrinsic difference between the substrate reactive and chelating functionalities in DTPA, such procedures can lead to cross-linking and denaturation of the antibody with concomitant degradation of its ability to bind to the target antigen.

In order to avoid the potential for such undesired cross-linking, bifunctional chelating agents incorporating a unique protein substrate reactive site have been developed. The first such compounds were derivatives of the compound ethylenediaminetetraacetic acid (EDTA). This compound comprises a backbone of two nitrogen atoms linked by an ethylene chain. Extending from the nitrogen atoms on the backbone are four carboxymethyl moieties which with the nitrogen atoms are suitable for metal binding. The bifunctional chelating derivatives of EDTA are characterized by the attachment of a unique protein substrate reactive function at a methylene carbon of the polyamine backbone. Sundberg, et al., J. Med. Chem. 17, 1304 (1974) discloses the synthesis of an EDTA derivative bearing a para-aminophenyl protein reactive substituent. This derivative may in turn be converted to bifunctional chelating agents capable of being coupled to protein substrates under mild conditions either by reaction of the amine with a portion of a chemically modified protein or by treatment of the primary amine to form other substituents capable of binding to protein substrates under mild conditions.

Meares, et al., J. Protein Chem., 3, 215-228 (1984) discloses methods whereby the para-aminophenyl derivative is converted to a diazonium derivative through nitrous acid treatment, to an isothiocyanate derivated by treatment with thiophosgene, to a bromoacetamide derivative by treatment with bromoacetylbromide and to a palmitaamidobenzyl derivative by treatment with palmitoyl chloride. Altman, et al., J. Chem. Soc. Perkin Trans. I., 365, 59-62 (1983) discloses a number of phenethyl analoques of the above EDTA compounds. See also, Sundberg, et al., U.S. Pat. No. 3,994,966.

Cyclic chelating agents are known in the art. Kroll, et al., Nature, 180 919-20 (1957) discloses the use of cyclohexane-1,2-trans-diaminetetraacetic acid for the removal of heavy metal ions from the human body. Moi, et al., Anal. Biochem., 148, 249-253 (1985) discloses a macrocyclic bifunctional chelating agent precursor named 6-(p-nitrobenzyl)-1,4,8,11-tetra-azacyclotetradecane N,N',N'',N'''-tetraacetic acid (p-nitrobenzyl-TETA) which forms a copper chelate which is extremely stable in human serum under physiological conditions. In addition, the p-bromoacetamidobenzyl derivative of TETA shows high stability after conjugation to a monoclonal antibody. The Moi, et al. reference also discloses that improved metal binding yields may be obtained in some cases where the conjugate contains a spacer group between the protein and TETA.

Of interest to the present application are the disclosures of Green, et al., Int. J. Nucl. Med. Biol., 12, 381-85 (1985) and Taliaferro, et al., Inorg. Chem. 23 1188-92 (1984) disclosing chelating agents. Green, et al. discloses a sexadentate ligand N,N'-dipyridoxylethylenediamine-N,N'-diacetic acid (PLED) complexed with gallium$^{68}$ and indium$^{111}$. Taliaferro, et al., discloses PLED chelates as well as those of N,N'-ethylene-bis[2-(o-hydroxy phenyl)glycine] (EHPG) and N,N'-bis(2-hydroxybenzyl) ethylenediamine-,N,N'-diacetic acid (HBED).

Other variations on known DTPA and EDTA derivatives include those of Brechbiel, et al., Inorg. Chem., 25, 2772-81 (1986) which discloses derivatives of DTPA wherein para-aminophenyl substituents are attached to the methylene carbons of the polyamine backbone. In addition, Altman, et al., J. Chem. Soc. Perkin Trans. I., 59 (1984) discloses a 2-carboxyethyl chelating derivative of EDTA.

Methods of synthesizing derivatives of DTPA and EDTA wherein the protein-reactive functionality is attached to a methylene carbon of the polyamine backbone are complex, difficult to practice and have limited flexibility. In addition, the polyamine backbone carbon atoms of many chelating agents such as those wherein such carbons are part of a cyclic system are not readily available for substitution. It is therefore desired to develop bifunctional chelating agents having a unique substrate reactive function attached to a moiety common to, and accessible in, all polyaminopolycarboxylate frameworks. It is further desired to develop general methods for the synthesis of such compounds.

Of interest to the present invention is the disclosure of Takeshita and Maeda, Yukagaku, 19, 984-93 (1970) which shows a surfactant compound with the structure:

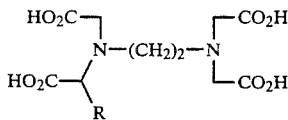

wherein R is a long-chain alkyl.

Also of interest to the present invention is the disclosure of Borch, et al., J. Amer. Chem. Soc., 93 2397 (1971) showing the reductive amination of a variety of pyruvic acids including phenylpyruvic and para-hydroxyphenylpyruvic acid to the corresponding dl-alpha amino acids under mild conditions using ammonia and sodium cyanoborohydride.

SUMMARY OF THE INVENTION

The present invention provides bifunctional chelating agents comprising a unique "substrate reactive" moiety incorporated into a carboxymethyl arm of a polyaminopolycarboxylate chelating framework capable of forming stable complexes with metal ions. Suitable substrate reactive groups include phenyl groups directly substituted or substituted through aliphatic spacer arms with substrate reactive moieties such as amino, thiocyanato, diazonium and bromoacetamide which are capable of reacting with one or more functionalities present on the substrate molecule to be labelled with a metal ion. The substrate reactive groups also comprise phenyl groups directly substituted or substituted through aliphatic spacer groups with substrate reactive moieties such as thiosemicarbazide and hydrazine.

The present invention is particularly advantageous in that it provides a general method for the introduction of a versatile substrate reactive moiety into any polyaminopolycarboxylic acid structure without compromising the metal binding properties of that structure. The prior art synthetic methods, whereby a substrate reactive moiety is introduced at a methylene carbon atom of the polyamine backbone, cannot readily be extrapolated to the synthesis of many other desired chelating agents such as those wherein these ethylene carbon atoms are part of a ring system. By providing compounds in which the substrate reactive function is attached at a moiety common to, and accessible in, all polyaminopolycarboxylate frameworks, the present invention provides a means for applying the full spectrum of chelating properties exhibited by such frameworks to problems involving the labelling of biologically active molecules with metal ions.

The bifunctional chelating agents of the invention are suitable for binding metals including radioactive metal ions to a variety of substrate molecules including, but not limited to proteins, glycoproteins, peptides, poly(amino acids), lipids, carbohydrates, polysaccharides, nucleosides, nucleotides, nucleic acids, bile acids, drugs, inhibitors and intact cells. Compounds according to the invention have as many as 10 or more metal binding substituents with the higher substituted compounds having improved stability when chelating metal ions with high coordination numbers such as lanthanide and actinide metals. The invention also provides cyclic bifunctional chelator systems which provide modified stability properties.

According to one aspect of the invention, antibody conjugates and antibody-metal ion conjugates are provided comprising the bifunctional chelating agents. In addition, the invention further provides in vivo diagnostic imaging methods utilizing radiation emitting and radiation absorbing metal ions. According to a further aspect of the invention, therapeutic methods are provided for treatment of conditions such as cancer whereby cytotoxic radiation emitting nuclides are bound to anti-tumor specific antigen antibodies by the chelating agents of the invention. The antibody-radionuclide conjugates according to the invention are then introduced into a subject and the cytotoxic radionuclides are selectively directed to cells bearing the tumor associated antigen.

BRIEF DESCRIPTION OF THE DRAWINGS

FIG. 1a is a graph showing the results of an ELISA assay comparing the degree of immune reactivity retained by an anti-CEA-DTTA(0.5) antibody conjugate compared with unconjugated anti-CEA.

FIG 1b is a graph showing the results of an ELISA assay comparing the degree of immune reactivity retained by an anti-CEA-DTTA(5.0) antibody conjugate compared with unconjugated anti-CEA.

FIG. 1c is a graph showing the results of an ELISA assay comparing the degree of immune reactivity retained by an anti-CEA-NCS-Compound A antibody conjugate compared with unconjugated anti-CEA.

DETAILED DESCRIPTION

The present invention provides bifunctional chelating agents comprising a unique substrate reactive moiety incorporated into a carboxymethyl arm of a polycarboxylate chelating framework which is capable of forming stable complexes with metal ions. The compounds of the invention are specifically characterized by having the structure:

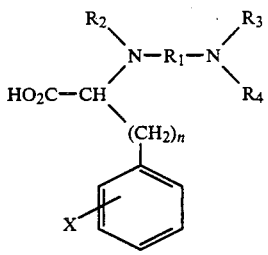

wherein X is meta or para and is nitro or a substrate reactive moiety;
wherein n=0 to about 10;
wherein R₁ is selected from the group consisting of:
- —(CH₂)$_q$,
- —[(CH₂)$_q$N(R₅)CH₂)$_r$],
- —[(CH₂)$_q$O(CH₂)$_r$O(CH₂)$_s$],
- [(CH₂)$_q$N(R₅)(CH₂)$_r$N(R₆)(CH₂)$_s$]

, and

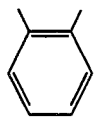

wherein q=2 or 3,
r=2 or 3, and
s=2 or 3;
wherein R₂, R₃, R₄ R₅ and R₆ are the same or different and are selected from the group consisting of:
- hydrogen
- CH₂CO₂H
- ortho-CH₂C₆H₄OH, and wherein when R₁=(CH₂)q
R₂ and R₃ may be fused to form a hydrocarbyl ring of the formula —(CH₂)$_t$N(R₇)(CH₂)$_u$N(R₈)(CH₂)$_v$— wherein t=2 or 3,
u=2 or 3, and
v=2 or 3
wherein R₇ and R₈ are selected from the group consisting of:
- hydrogen,
- —CH₂CO₂H, and
- ortho-CH₂C₆H₄OH.

While the present invention provides numerous bifunctional chelating agents comprising a variety of substrate reactive moieties and chelating functionalities of various sizes, shapes and denticities, there is no single preferred chelating agent according to the invention. Preferred compounds vary according to the specific nature of the substrate and metal ion to be bound. Nevertheless, particular substituents and formations tend to be generally preferred under particular circumstances.

When X is nitro, it is understood that further conversion to a substrate reactive moiety is required prior to reaction with a substrate.

Preferred substrate reactive groups for X include those selected from the group consisting of:

| | |
|---|---|
| —NH₂, | (AMINO) |
| —NN⁺, | (DIAZONIUM) |
| —NCS, | (ISOTHIOCYANATE) |
| —NCO, | (ISOCYANATE) |
| —NHNH₂ | (HYDRAZINE) |
| —NHCONHNH₂, | (SEMICARBAZIDE) |
| —NHCSNHNH₂, | (THIOSEMICARBAZIDE) |
| —NHCOCH₂Cl, | (CHLOROACETAMIDE) |
| —NHCOCH₂Br, | (BROMOACETAMIDE) |
| —NHCOCH₂I, | (IODOACETAMIDE) |
| —N₃, | (AZIDE) |
| —NHCONH(CH₂)$_m$NH₂, | (AMINOALKYLUREA) |
| —NHCSNH(CH₂)$_m$NH₂, | (AMINOALKYLTHIOUREA) |
| 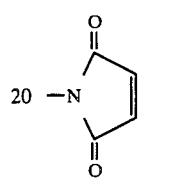 | (MALEIMIDE) |
| 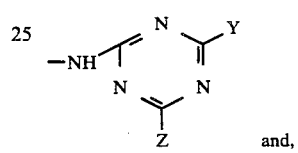 and, | (HALOTRIAZINE) |
| —NHCSNH—⌬—B(OH)₂ | (META-(DIHYDROXYBORYL)PHENYLTHIOUREA) | wherein Y is selected from the group consisting of Cl, Br and F;
wherein Z is selected from the group consisting of Cl, Br, F, OH and OCH₃;
wherein m=1 to about 10.

Particularly preferred substrate reactive moieties include those wherein X is para substituted and is selected from the group consisting of: —NH₂, —NCS, —NHCOCH₂Br and —NHCSNH(CH₂)₂NH₂. Where it is desired to avoid direct linkage with the amino acid side chain of a protein substrate, preferred substrate reactive moieties include those which are capable of reaction with glycosylation present on some proteins. Because such glycosylation is generally inert, it must often be derivatized or oxidized to increase its reactivity. Substrate reactive moieties preferred for use in binding glycosylated proteins include —NHNH₂ and —NHCSNHNH₂.

Preferred substituents for R₁ include those selected from the group consisting of:
- —(CH₂)—
- —[(CH₂)₂N(CH₂CO₂H)(CH₂)₂]—
- —[(CH₂)₂O(CH₂)₂O(CH₂)₂]—
- [(CH₂)₂N(CH₂CO₂H)(CH₂)₂N(CH₂CO₂H)(CH₂)₂]

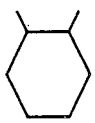

and

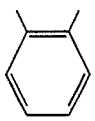

Substituents $R_2$, $R_3$, $R_4$, $R_5$, $R_6$, $R_7$ and $R_8$ are preferably selected from the group consisting of hydrogen and $CH_2CO_2H$. Preferred compounds for certain applications include those wherein $R_2$ and $R_3$ are not fused to form a hydrocarbyl ring and wherein $R_2$, $R_3$, $R_4$, $R_5$ and $R_6$ are selected from the group consisting of hydrogen and $CH_2CO_2H$. Particularly preferred for certain applications are those compounds wherein $R_2$, $R_3$, $R_4$ and $R_5$ are $CH_2CO_2H$.

Preferred compounds further include those wherein $n=1$. Particularly preferred for certain applications are chelating agents wherein $R_1$ is —[$CH_2$—$CH_2$]— or —[($CH_2$)$_2$N($CH_2CO_2H$)($CH_2$)$_2$]— and X is NCS. A particularly preferred group of compounds includes those wherein X is para and is selected from the group consisting of —$NO_2$, —$NH_2$, —NCS, —$NHCSNHNH_2$ and —$NHCSNH(CH_2)_2NH_2$ wherein $n=1$, wherein $R_1$ is selected from the group consisting of —($CH_2$)$_2$—,
—[($CH_2$)$_2$O($CH_2$)$_2$O($CH_2$)$_2$]—,
—[($CH_2$)$_2$N($CH_2CO_2H$)($CH_2$)$_2$]—

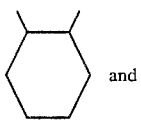 and wherein $R_2$, $R_3$, $R_4$ are —$CH_2CO_2H$.

A preferred compound with a denticity of 3 is defined by the structure:

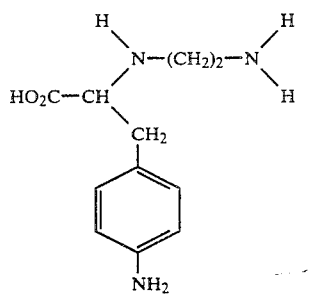

N-(2-aminoethyl)-(4-aminophenyl)alanine

Even while certain substituents and moieties of the chelating compounds of the invention are generally preferred, the specific structures of the compounds of the invention vary widely according to the natures of the substrate and the metal ion to be bound. Nevertheless, certain general principles may be applied to tailoring the compounds of the invention to specific uses. For example, certain metal ions such as members of the actinide and lanthanide series of metals have large radii and prefer high coordination numbers. Preferred chelating agents for binding with such ions are larger compounds with increased denticity. As another example, the precise location of particular amino acid residues in the structure of a protein (on or near an active site of an enzyme, or on or near the recognition region of an antibody), may require the selection of an alternative substrate reactive moiety on a chelating agent. It may also occur that macrocyclic chelating agents according to the invention may provide improved stability characteristics for binding of certain metal ions. Accordingly, multiple aspects of the present invention are subject to variation.

Aliphatic chain lengths may be varied within the core structure and denticity may be increased by the incorporation of metal reactive carboxymethylamino groups on the $R_1$ chain. Chelating agents according to the invention comprising increasing levels of denticity include N-(carboxymethyl)-N-(2-(bis(carboxymethyl)amino)ethyl)-(4-aminophenyl)alanine (hereinafter "$NH_2$-Compound A") with a denticity of 6, N-(carboxymethyl)-N-(2-aminoethyl)-N'-(carboxymethyl)-N'-(2'-(bis(carboxymethyl)amino)ethyl)-(4-aminophenyl)alanine (hereinafter "$NH_2$-Compound B") with a denticity of 8, and N-(carboxymethyl)-N-(2-aminoethyl)-N'-(carboxymethyl)-N'-(2'-aminoethyl)-N''-(carboxymethyl)-N''-(2''(bis(carboxymethyl)amino)ethyl)-(4-aminophenyl)alanine with a denticity of 10.

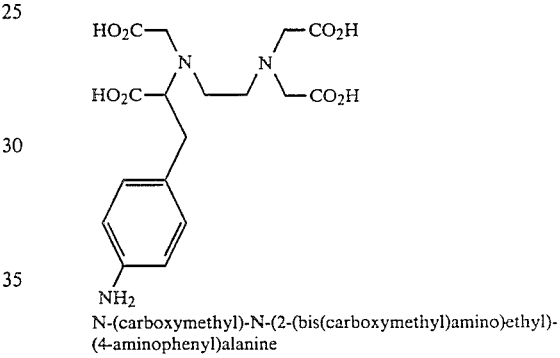

N-(carboxymethyl)-N-(2-(bis(carboxymethyl)amino)ethyl)-(4-aminophenyl)alanine

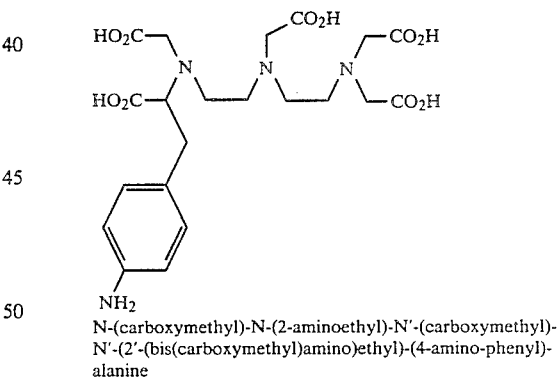

N-(carboxymethyl)-N-(2-aminoethyl)-N'-(carboxymethyl)-N'-(2'-(bis(carboxymethyl)amino)ethyl)-(4-amino-phenyl)-alanine

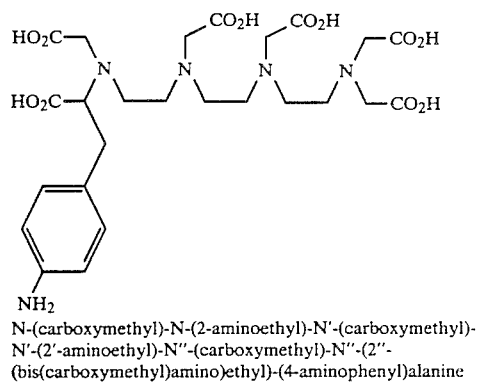

N-(carboxymethyl)-N-(2-aminoethyl)-N'-(carboxymethyl)-N'-(2'-aminoethyl)-N''-(carboxymethyl)-N''-(2''-(bis(carboxymethyl)amino)ethyl)-(4-aminophenyl)alanine Such chelating agents with increasing denticities ranging from about 6 to 10 or more are particularly useful for chelating metals which favor high coordination numbers such as members of the lanthanide and actinide series.

The $R_1$ group may also be selected so as to introduce steric constraints into the diamine backbone by making the backbone part of a ring system. The introduction of such steric constraints in either non-aromatic or aromatic ring form leads to modified stability for certain metal complexes. Chelating agents according to the invention wherein the backbone has been so modified include N-(carboxymethyl)-N-trans-(2-(bis (carboxymethyl)amino) cyclohexyl)-(4-nitrophenyl)alanine, with a denticity of 6, and N-(carboxymethyl)-N-(2-(bis(carboxymethyl)amino) phenyl)-(4-nitrophenyl)alanine, with a denticity of 6.

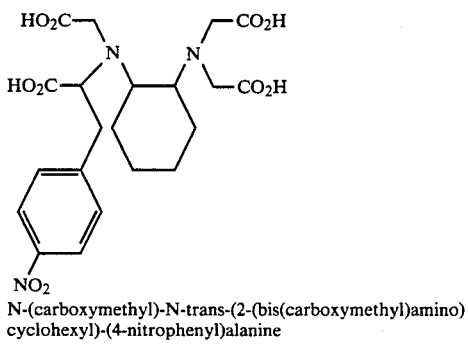

N-(carboxymethyl)-N-trans-(2-(bis(carboxymethyl)amino) cyclohexyl)-(4-nitrophenyl)alanine

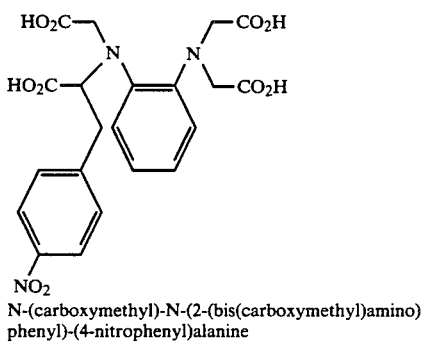

N-(carboxymethyl)-N-(2-(bis(carboxymethyl)amino) phenyl)-(4-nitrophenyl)alanine

Further useful variants of the $R_1$ group include chelators in which $R_1$ contains additional donor atoms capable of forming a coordinate bond with the metal center. One such chelating agent according to the present invention is N-(1-carboxy-2-(p-nitrophenyl)-ethyl)-1,8-diamino-3,6-dioxaoctane-N,N′,N′-triacetic acid.

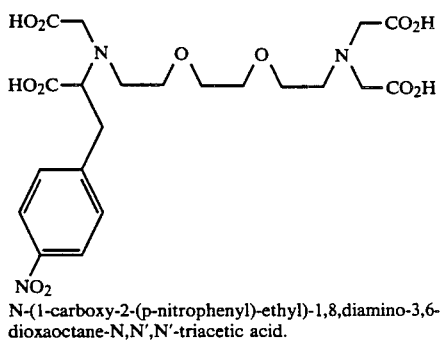

N-(1-carboxy-2-(p-nitrophenyl)-ethyl)-1,8,diamino-3,6-dioxaoctane-N,N′,N′-triacetic acid.

In this structure, the two ether oxygen atoms can participate in metal binding, together with the two amine nitrogen atoms and the four carboxylate oxygen atoms, leading to an overall denticity of eight.

The present invention further provides compounds wherein one or more carboxymethyl groups in the polyaminopolycarboxylate chelator are replaced by ortho-hydroxybenzyl groups. Such substituents comprise a metal binding moiety and present appropriate stereochemistry for chelation. N-((2-hydroxyphenyl)-methyl)-N-(2-aminoethyl)-N′-((2′-hydroxyphenyl)-methyl-N′-(carboxymethyl)-(4-aminophenyl)alanine with a denticity of 6 comprises an appropriate example of such a compound. Such a structure is believed to provide for improved stability of indium complexes relative to chelating agents of the prior art.

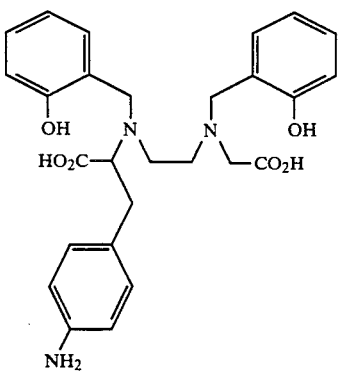

N-((2-hydroxyphenyl)methyl)-N-(2-aminoethyl)-N′-((2′-hydroxyphenyl)methyl)-N′-(carboxymethyl)-(4-aminophenyl)alanine The present invention also comprises macrocyclic chelating agents wherein $R_2$ and $R_3$ may be fused to form a hydrocarbyl ring. Such macrocyclic chelating agents provide modified stability properties which may be desirable for certain applications. A compound exemplary of such macrocyclic chelating agents is N-((α-(3-(4-aminophenyl)propyl))carboxymethyl)-N′,N″,N‴-(carboxymethyl)-1,4,8,11-tetraazacyclotetradecane shown below.

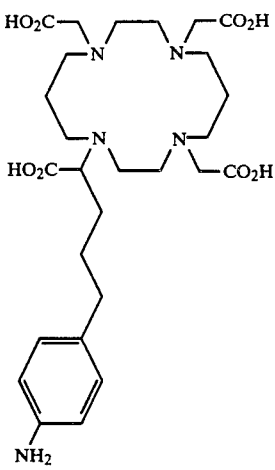

METAL IONS

Metal ions which may be chelated according to the invention include gamma emitter isotopes which are useful for diagnostic scintigraphy. Indium[111] with a half-life of 2.8 days is particularly useful while other suitable gamma emitters include gallium$^{67}$, gallium$^{68}$ and technetium$^{99m}$. Materials according to the invention may be chelated to beta radiation emitters which are useful as cytotoxic agents for radiotherapy. Such emitters include isotopes such as scandium$^{46}$, scandium$^{47}$, scandium$^{48}$, copper$^{67}$, gallium$^{72}$, gallium$^{73}$, yttrium$^{90}$, ruthenium$^{97}$, palladium$^{100}$, rhodium$^{101m}$, palladium$^{109}$, samarium$^{153}$, rhenium$^{186}$, rhenium$^{188}$, rhenium189, gold$^{198}$, radium$^{212}$ and lead$^{212}$.

The chelating agents of the invention may also be used to bind alpha radiation emitting materials such as bismuth$^{212}$, positron emitters such as gallium$^{68}$ and zirconium$^{89}$, fluorescent members of the lanthanide series of elements such as terbium and europium and of the transition series such as ruthenium and paramagnetic materials such as gadolinium and iron. In addition the agents of the invention are also suitable for binding numerous other metal ions which may be useful for a variety of purposes, including those in which a catalytic property of the metal ion is of utility. Iron, copper, vanadium, rhodium, platinum, palladium and titanium are examples of metal ions useful in catalyzing a variety of organic reactions, such as the cleavage of nucleic acids by the iron-catalyzed generation of hydroxyl free radicals.

COMPLEXING OF METAL IONS

Methods for forming chelating agent/metal ion conjugates are well known to those of skill in the art. Complexes of the chelating agent and metal ions may generally be formed by incubation of the chelating agent/substrate conjugate with the metal ion in a buffered solution in which the conjugate is physiologically stable. Suitable buffers include those with weak metal-binding properties, such as citrate, acetate or glycine. Appropriate concentrations, temperatures and pH may be selected by one of skill in the art to ensure metal ions bind to the chelating functionality rather than weak metal binding sites on the substrates. It is particularly desired that all solutions be maintained free of metal impurities. After incubation for an appropriate period of time, unbound metal ions may be separated, if necessary, from the substrate/chelating agent/metal ion conjugate by a procedure such as gel filtration.

SUBSTRATE REACTIVE FUNCTIONALITIES

The substrate reactive moieties according to the present invention comprise those moieties capable of a specific binding reaction with at least one functionality present in a substrate molecule which may be a biologically active substrate. If the substrate is a protein, such moieties may be reactive with side chain groups of amino acids making up the polypeptide backbone. Such side chain groups include the carboxyl groups of aspartic acid and glutamic acid residues, the amino groups of lysine residues, the aromatic groups of tyrosine and histidine and the sulfhydryl groups of cysteine residues.

Carboxyl side groups presented by a substrate such as a polypeptide backbone may be reacted with amine substrate reactive groups of the compounds of the invention by means of a soluble carbodiimide reaction. Amino side groups presented by a substrate may be reacted with the isothiocyanate, isocyanate or halotriazine derivatives of this invention to effect linkage of the chelator to the polypeptide. Alternatively, amino side groups on the substrate may be linked to compounds of this invention bearing amine substrate reactive groups by means of bifunctional agents such as dialdehydes and imidoesters. Aromatic groups presented by a substrate may be coupled to the chelating agents of this invention via the diazonium derivative. Sulfhydryl groups on substrate molecules may be reacted with maleimides or with haloalkyl substrate reactive groups such as iodoacetamide. Free sulhydryl groups suitable for such reactions may be generated from the disulfide bonds of protein immunoglobulins or may be introduced by chemical derivatization. Linkage to free sulfhydryl groups generated in the intra-heavy chain region of immunoglobulins does not interfere with the antigen binding site of the immunoglobulin but may render the antibody incapable of activating complement.

When the substrate is a glycosylated protein, an alternative to forming a linkage to the compounds of the present invention via the polypeptide backbone is to form a covalent linkage with the carbohydrate side chains of the glycoprotein according to the methods such as those of McKearn, et al., EPO 88,695. Thus, the carbohydrate side chains of antibodies may be selectively oxidized to generate aldehydes which may then be reacted either with amine substrate reactive groups to form a Schiff base or with hydrazine, semicarbazide or thiosemicarbazide substrate reactive groups, to give the corresponding hydrazone, semicarbazone or thiosemicarbazone linkages. These same methods may also be employed to link the bifunctional chelators of this invention to non-proteinaceous substrates such as carbohydrates and polysaccharides.

An alternative substrate reactive moiety useful for linkage to carbohydrates and polysaccharides without the necessity for prior oxidation is the dihydroxyboryl moiety, such as is present in the meta-(dihydroxyboryl)-phenylthiourea derivatives of the present invention. This moiety is reactive with substrates containing a 1,2-cis-diol, forming a 5-membered cyclic borate ester, and thus is of use with those carbohydrates, polysaccharides and glycoproteins which contain this group. The dihydroxyboryl derivatives may also be used to link the chelators of this invention to ribonucleosides, ribonucleotides and ribonucleic acids, since ribose contains a 1,2-cis-diol group at the 2′, 3′ position, as disclosed by Rosenberg, et al., Biochemistry, 11, 3623–28 (1972). Deoxyribonucleotides and DNA substrates may not be linked to the present chelators in this fashion as the 3′ hydroxyl group is absent. The latter substrates may, however, be conjugated to isothiocyanate derivatives of chelators by first forming an allylamine derivative of the deoxyribonucleotide as disclosed by Engelhardt, et al., EPO 97,373.

When the substrate to be linked with the chelators of this invention is an intact cell, either polypeptide-reactive or carbohydrate-reactive moieties may be employed. Hwang and Wase, Biochim. Biophys. Acta, 512, 54–71 (1978), disclose the use of the diazonium derivative of the bifunctional EDTA chelator of Sundberg, et al., J. Med. Chem., 17, 1304 (1974), to label erythrocytes and platelets with indium-111. The dihydroxyboryl moiety is reactive with a variety of bacteria, viruses and microorganisms, see Zittle, Advan. Enzym., 12 493 (1951) and Burnett, et al., Biochem. Biophys. Res. Comm., 96, 157–62 (1980).

According to the present invention, substrate reactive moieties include amino (—NH$_2$), diazonium (—NN+), isothiocyanate (—NCS), isocyanate (—NCO), hydrazine (—NHNH$_2$), semicarbazide (—NHCONHNH$_2$), thiosemicarbazide (—NHCSNHNH$_2$), haloacetamide (—NHCOCH$_2$X) including chloro-, bromo- and iodoacetamide, azide (—N$_3$), aminoalkylurea (—NHCONH(CH$_2$)$_m$NH$_2$), aminoalkylthiourea (—NHCSNH(CH$_2$)$_m$NH$_2$), wherein m is from 1 to about 10, maleimide, halotriazine including chloro-, bromo- and iodotriazine and meta-(dihyroxyboryl)phenylthiourea (—NHCSNHC$_6$H$_4$B(OH)$_2$). Other reactive moieties which may be suitable for linking the chelating agents to substrates include disulfides, nitrenes, sulfonamides, carbodiimides, sulfonyl chlorides, benzimidates, —COCH$_3$ and —SO$_3$H. The preferred substrate reactive moiety for any particular application of this invention will be dictated by the nature of the substrate and by its susceptibility to loss of biological activity as a consequence of forming a given type of linkage. By definition, the formation of any given linkage involves a chemical transformation of the substrate reactive moiety, X, into the conjugated form of that moiety (hereafter the "residue" of X).

The reactive moieties of the invention are oriented at the meta or preferably para position on a phenyl group which is attached by means of an aliphatic spacer group to one of the carboxymethyl arms of the polyaminopolycarboxylate chelating framework of the invention. The spacer group may consist of from one to about ten carbon atoms, and may be linear or branched alkyl or substituted alkyl provided such branching or substituents do nct interfere with the metal binding sites or substrate reactive groups. Linear alkyl linkers are nevertheless preferred with Cl alkyl linkers particularly preferred.

SUBSTRATES USEFUL WITH THE PRESENT INVENTION

Substrate molecules which may be reacted with the chelating agents of the present invention include proteins, glycoproteins, peptides, poly(amino acids), lipids, carbohydrates, polysaccharides, nucleosides, nucleotides, nucleic acids, bile acids, drugs, inhibitors or intact cells. Suitable proteins include immunoglobulins, antigens, enzymes, components of the blood coaqulation-/anti-coaqulation system and various biochemically active molecules and receptors. Such proteins may be derived, for example, from genetically manipulated cells. According to one embodiment of the present invention, the bifunctional chelating agents may be used to bind various types of antibodies including IgA, IgD, IgE, IgG and IgM. The antibodies may be directed against a variety of antigenic determinants including those associated with tumors, histocompatibility and other cell surface antigens, bacteria, fungi, viruses, enzymes, toxins, drugs and other biologically active molecules. Antigens associated with tumors for which antibodies may be specifically reactive include such antigens as are described in Zalcberg and McKenzie, J. Clin. Oncology, Vol. 3; pp. 876–82 (1985) and include, but are not limited to, carcinoembryonic antigen (CEA), mucins such as TAG-72, human milk fat globule antigens and receptors such as the IL-2 and transferrin receptors. Such antibodies may be monoclonal or polyclonal or made by recombinant techniques such as described in Morrison, et al., Proc. Nat. Acad. Sci. U.S.A. 81, 6851–55 (1984).

Fragments of antibody molecules may also be bound including half antibody molecules and Fab, Fab' or F(ab')$_2$ fragments. Nicolotti, EPO 174,853 published Mar. 19, 1986 hereby incorporated by reference, discloses methods by which entire antibodies are treated to effect a site specific cleavage of the two heavy chains, removing the F$_c$ portion at the carboxyl terminal ends of the heavy chains.

Substrates are reacted with the substrate reactive moieties of the chelating agents according to the methods disclosed above. Each substrate may be bound by more than one chelating agent as may be desired. The maximum extent of substitution on a substrate such as a protein, however, is limited by the nature of glycosylation on the protein or the number and location of reactive amino acid side chains on the molecule. Where, as with antibodies, it is desired that the conjugated protein retain its biological activity, the extent of substitution will be limited according to the nature and position of target glycosylation or amino acid residues both in the primary as well as in the tertiary sequence of the protein and their degree of involvement in the antigen binding site.

Other substrates contemplated by this invention include polysaccharide matrices which, when derivatized with chelators, provide means for the extraction of metals from metalloproteins and other metal containing substrates and for the affinity chromatography of proteins by the methods of porath and Olin, Biochemistry, 22, 1621–30 (1983). Nucleic acids linked to the chelators of this invention may be used to monitor any nucleic acid hybridization reaction, as described by Engelhardt, et al., EPO 97,373. Bifunctional chelators linked to drugs may be used to follow the uptake of that drug into tissues, as exemplified by use of the antibiotic drug bleomycin linked to the bifunctional EDTA derivative of Sundberg, et al., J. Med. Chem., 17, 1304 (1974), as a means of imaging tumors, see DeRiemer, et al., J. Med. Chem., 22, 1019–23 (1979); Goodwin, et al., J. Nucl. Med., 22, 787–92 (1981). In addition to drugs, other low melecular weight substances that target a particular organ system may similarly be used to image that system. Thus cholic acid, which is known to target the hepatobiliary system in man, as described by Boyd et al., J. Nucl. Med., 22, 720–725 (1981), may be used to image that system when conjugated to a bifunctional chelator of this invention and labeled with either a gamna-emitting radiometal (for radioscintigraphic detection) or with a paramagnetic metal such a gadolinium (for detection by means of Magnetic Resonance Imaging). Intact cells, such as erythrocytes and platelets, have been labelled with radioisotopic metals by linkage to bifunctional chelators, as described by Hwang and Wase, Biochim, Biophys. Acta, 512, 54–71 (1978), and such labelled cells may be used to detect areas of abnormal accumulation in the body. Linkage of the compounds of this invention to low molecular weight substances which themselves undergo a specific binding reaction with a macromolecular biological molecule are contemplated. Haner, et al., Arch. Biochem. Biophys., 231 477–86 (1984), disclose methods for linking EDTA to p-aminobenzamidine, a specific inhibitor of trypsin which binds strongly in the active site, providing an affinity label of use in probing that site. Schultz and Dervan, J. Amer. Chem. Soc., 105 7748–50 (1983), disclose the sequence-specific double strand cleavage of DNA by iron complexes of conjugates formed by linking EDTA to distamycin, an N-methylpyrrole tripeptide which binds to DNA in a sequence-specific manner.

The following examples illustrate methods for synthesis of various chelating agents according to the invention. Examples 1 through 5 describe the synthesis of N-(carboxymethyl)-N-(2-(bis(carboxymethyl)amino)ethyl)-(4-aminophenyl)alanine (NH₂-Compound A) and analogs presenting alternative substrate reactive groups. Examples 6 and 7 describe syntheses of N-(carboxymethyl)-N-(2-aminoethyl)-N'-(carboxymethyl)-N'-(2'-(bis(carboxymethyl)amino)ethyl)-(4-aminophenyl)alanine NH₂-Compound B and its 4-isothiocyanatophenyl analoque. Example 8 describes synthesis of N-(carboxymethyl)-N-(trans-(2-(bis(carboxymethyl)amino)cyclohexyl)-(4-nitrophenyl) alanine.

In examples 9 and 10, the 4-isothiocyanatophenyl chelating agent of example 3 was linked to an anti-CEA monoclonal antibody and the conjugate was compared with DTTA conjugates according to the prior art. In example 11, the 4-isothiocyanatophenyl chelating agent of example 7 was conjugated to an anti-CEA monoclonal antibody and evaluated according to the methods of example 9. In example 12, the anti-CEA monoclonal antibodies of example 9 were cleaved to provide F(ab')2 fragments which were conjugated to the chelating agent of example 3. In example 13, the chelating agent of example 3 was conjugated to monoclonal antibody B72.3 which is specifically reactive with a tumor-associated glycoprotein (TAG-72).

In example 14, the 4-(2-aminoethylthiourea)-phenyl chelating agent of example 5 was conjugated with polyglutamic acid. In examples 15, 16, 17 and 18, biodistribution studies were conducted with the antibody conjugates of examples 9, 11, 12 and 13, respectively.

Example 19 describes the synthesis of N-(1-carboxy-2-(p-nitrophenyl)-ethyl)-1,8-diamino-3,6-dioxaoctane-N,N',N'-triacetic acid, an 8-coordinate chelator presenting two ether oxyten donors in addition to the nitrogen and carboxylate binding sites.

Example 20 describes the preparation of a conjugate formed between the bifunctional chelator of example 5 and cholic acid. In example 21, the conjugate of example 20 was labeled with indium-111 and biodistribution studies were conducted in mice. Example 22 describes a gamma camera imaging study in which the indium-111 labeled conjugate of example 21 was used to image the hapatobiliary system of a rabbit.

EXAMPLE 1

In this example, N-(carboxymethyl)-N-(2-(bis (carboxymethyl)amino)ethyl)-(4-nitrophenyl)alanine (NO₂-Compound A), a para-nitrophenyl substituted bifunctional chelating agent presenting two amine and four carboxymethyl metal reacting groups according to the invention, was synthesized by carboxymethylation of the monosubstituted diamine obtained on reductive amination of 4-nitrophenylpyruvic acid with ethylenediamine.

In order to produce the 4-nitrophenylpyruvic acid, the azalactone, 5-keto-2-methyl-4-(4'-nitrobenzylidine)-4,5-dihydro-oxazole was first produced by reaction at 100° C. for 2 hours of a solution comprising 7.0 grams (60 mmol) of N-acetylglycine in 20 ml of acetic acid and 9.7 grams (64 mmol) of 4-nitrobenzaldehyde (Aldrich Chemical Co., Milwaukee, Wis.) and 14.4 grams (176 mmol) sodium acetate in 21 ml of acetic anhydride. After cooling the mixture to 10° C., 100 ml of water was added with vigorous stirring and 12.9 grams of the azalactone was collected by filtration.

In the next step, 7.9 grams (34 mmol) of 5-keto-2-methyl-4-(4'-nitrobenzylidine)-4,5-dihydro-oxazole was dissolved in 200 ml of acetic acid and was heated to 100° C. Five ml of water was then added and the mixture was stirred at 100° C. for an additional 15 minutes. The solution was then allowed to cool slowly to room temperature and 7.2 grams of α-acetamino-4-nitrocinnamic acid were then isolated.

A suspension comprising 7.2 grams (29 mmol) of α-acetamino-4-nitrocinnamic acid in 50 ml of 3 M HCl was stirred at reflux for 7 hours. The mixture was then cooled to 0° C. and 5.4 grams of the resulting 4-nitrophenylpyruvic acid was collected by filtration, washed with cold H₂O and dried under vacuum.

A solution comprising 15 grams (71.7 mmol) of 4-nitrophenylpyruvic acid in 500 ml methanol was added to a solution comprising 11.6 grams (87.2 mmol) ethylene-diamine dihydrochloride in 100 ml water. The pH of the resulting mixture was then brought to 6.0 using 7 M sodium hydroxide. To the mixture was then added 7.86 grams (125 mmol) of sodium cyanoborohydride and the pH was readjusted to 6.0 using 6 M HCl. The mixture was stirred at room temperature for 3 days and then 30 ml of concentrated HCl was added. After stirring for an additional 30 minutes, the solution was evaporated under vacuum until an orange residue was recovered: this was suspended in 250 ml of H₂O and washed with ethyl acetate (5 ×200 ml). The yellow aqueous layer was evaporated under vacuum leaving a yellow-white residue which was identified as crude N-(2-aminoethyl)-(4-nitrophenyl)alanine dihydrochloride. The crude product was chromatographed on a Dowex 50X2-200 (H+ form) ion exchnage column, eluting initially with 700 ml of H₂O and then with a 5% (v/v) solution of ammonium hydroxide. Ultraviolet light absorbing ninhydrin-positive fractions were combined and evaporated under vacuum to provide a residue which was dissolved in ethanol. Addition of concentrated HCl to the solution caused precipitation of a dense white precipitate which was collected by filtration, washed with ethanol and diethyl ether and air dried to provide 6.56 grams of N-(2-aminoethyl)-(4-nitrophenyl) alanine dihydrochloride.

Three grams (9.20 mmol) of the purified N-(2-aminoethyl)-(4-nitrophenyl)alanine dihydrochloride was then added to a solution comprising 4.51 grams (32.5 mmol) of bromoacetic acid in 25 ml of water and the mixture was heated to 45° C. The pH of the reaction mixture was brought to 10 by adding 7 M NaOH and the mixture was stirred at 45° C. for 20 hours while the pH was maintained at 10 by periodic addition of 7 M NaOH.

While intramolecular condensation leading to lactam formation did not present a problem during the reductive amination step to yield the diamine, the high temperatures used in the carboxymethylation reaction lead to formation of a lactam identified as a N,N'-bis(carboxymethyl) derivative. For this reason the cooled product was chromatographed to remove the lactam impurity on a Bio-Rad AGI-X4 (formate form) ion exchange column (Bio-Rad, Richmond, Calif.) by eluting successively with one liter each of water, 3.5 M formic acid and 6.0 M formic acid. The fractions were then evaluated by HPLC on a Waters Delta Prep 3000 system using a Waters μ-Bondpak C-18 column (0.39×30 cm) with 20% methanol and 0.01 M triethylamine in acetic acid as a mobile phase. This analysis found the lactam eluting with the 3.5 M formic acid and the desired product eluting with the 6.0 M formic acid. Fractions containing the product were then combined and evaporated to dryness to yield 1.79 grams of N-(carboxymethyl)-N-(2-(bis(carboxymethyl) amino)ethyl)-(4-nitrophenyl)alanine.

EXAMPLE 2

In this example, the 4-nitrophenyl substituted chelating agent of the invention produced according to example 1 was converted to a 4-aminophenyl substituted compound. A solution comprising 0.91 grams (2.13 mmol) of N-(carboxymethyl)-N-(2-(bis(carboxymethyl)amino) ethyl)-(4-nitrophenyl)alanine produced according to example 1, 100 ml of water and 15 ml of formic acid was hydrogenated in a Parr (Model 3911, Moline, Ill.) hydrogenator at room temperature and 35 psi for 2 hours in the presence of 0.10 grams of 10% palladium on carbon as catalyst. The mixture was then filtered through celite to remove catalyst and the filtrate was evaporated to dryness. The resulting residue was then dissolved in 50 ml of 4 M HCl and lyophilized to yield 0.87 grams of the 4-aminophenyl substituted compound, N-(carboxymethyl)-N-(2-(bis(carboxymethyl)amino) ethyl)-(4-aminophenyl)-alanine trihydrochloride.

EXAMPLE 3

In this example, the 4-aminophenyl chelating agent of example 2 was reacted to form the corresponding 4-isothiocyanatophenyl chelating agent. Following the procedure of Meares, et al., Anal. Biochem., 142, 68–78 (1984), 0.68 grams (1.34 mmol) of the 4-aminophenyl product of example 2 was dissolved in 12 ml of 3 M HCl. To this was added 1.70 ml of 85% thiophosgene/CCl4 (v/v) (18.95 mmol), and the resulting suspension stirred for 6 hours at room temperature. A 15 ml aliquot of diethylether was then added and the white precipitate formed was filtered off and dried under vacuum, to give 0.38 grams of the 4-isothiocyanatophenyl substituted compound, N-(carboxymethyl)-N-(2-(bis(carboxymethyl) amino)ethyl)-(4-isothiocyanatophenyl) alanine dihydrochloride.

EXAMPLE 4

In this example, the 4-isothiocyanatophenyl chelating agent of example 3 was reacted to form the corresponding 4-thiosemicarbazidophenyl chelating agent. According to this procedure, 0.15 grams of the 4-isothiocyanatophenyl product (0.29 mmol) was suspended in 15 ml of water and cooled in an ice bath. To this suspension was then added 0.255 ml of triethylamine and 0.066 ml of 85% hydrazine hydrate (1.75 mmol) and the resulting mixture was stirred in the ice bath for 2 hours and then at room temperature for a further 1 hour. The mixture was evaporated to dryness under vacuum and the residue dissolved in 20 ml of 4 M HCl. This solution was again evaporated to dryness under vacuum and the resulting residue was chromatographed on a Bio-Rad AG1-X4 ion exchange column (chloride form), eluting successively with 100 ml each of water and 4 M HCl. The 4 M HCl eluate was evaporated to dryness under vacuum to yield 0.15 grams of N-(carboxymethyl)-N-(2-(bis(carboxymethyl)amino)ethyl)(4 -thiosemicarbazidophenyl)alanine trihydrochloride in the form of a white solid.

EXAMPLE 5

In this example, the 4-isothiocyanatophenyl chelating agent of example 3 was converted to the corresponding 4-(2-aminoethylthiourea)phenyl derivative, providing a reactive aliphatic amine group linked to the phenylthiourea substituent by a 2-carbon spacer.

First, a mono-protected ethylenediamine derivative was prepared by adding a solution of 6.0 grams of di-t-butyldicarbonate (27.5 mmol) in 300 ml of THF dropwise over 3 hours to a stirred solution of 40.5 grams of ethylenediamine (674 mmol) in 150 ml of methanol which was cooled in an ice bath. The resulting mixture was stirred in the ice bath for a further 1 hour, then was warmed to room temperature. The residue obtained on evaporation of this solution to dryness was then chromatographed on a silica column (Kieselgel, 70–230 mesh, E. Merck, Darmstadt, W. Germany) eluted with (20:0.5:79.5) methanol:ammonium hydroxide:methylene chloride. Fractions containing the desired product were identified by thin layer chromatography on silica plates (Whatman Co., Clifton, N.J.) developed in the same solvent mixture used to elute the column ($R_f$=0.6). These fractions were combined and evaporated to dryness under vacuum to yield 4.1 grams (93%) of N-(t-butoxycarbonyl)ethylenediamine in the form of a yellow oil.

In the next step, a solution of 0.39 grams of N-(t-butoxycarbonyl)ethylenediamine (2.4 mmol) in 5 ml of DMF was added to a mixture of 0.34 grams of the 4-isothiocyanatophenyl product of example 3 (0.66 mmol) and 0 35 ml of triethylamine (2.5 mmol) in 7 ml of DMF cooled to 0° C. The resulting mixture was stirred at 0° C. for a further 15 minutes and then at room temperature for 48 hours. At that point, 2 ml of water were added and the mixture stirred for a further 6 hours then evaporated to dryness under vacuum. The residue was dissolved in 20 ml of water and this solution was washed with three 25 ml aliquots of methylene chloride. The aqueous layer was then lyophilized and the resulting tan-colored solid chromatographed on a Bio-Rad AG1-X4 column (formate form) eluted successively with 150 ml of water, 200 ml of 3.5 M formic acid and 200 ml of 7 M formic acid. The 7 M formic acid eluate was evaporated to dryness to yield 0.23 grams (58%) of N-(carboxymethyl)-N-(2-(bis(carboxymethyl)amino) ethyl)-(4-(N'-(2'-(N''-t-butoxycarbonyl))aminoethylthiourea) phenyl)alanine. 0.17 grams of this material (0.28 mmol) were then de-protected by stirring in 5.0 ml of trifluoroacetic acid at room temperature for 6 hours, protected from atmospheric moisture. The solvent was then evaporated, the residue dissolved in 10 ml of 2 M HCl and this solution was evaporated to dryness under vacuum. The resulting residue was chromatographed on a Bio-Rad AG1-X4 column (formate form) eluted successively with 100 ml of water then 50 ml each of 1 M, 2 M, 3 M and 4 M formic acid. Ultraviolet-absorbing fractions from the formic acid eluates were combined and evaporated to dryness under vacuum. The resulting residue was dissolved in 100 ml of 4 M HCl and evaporated to dryness under vacuum to yield 0.14 grams (81%) of N-(carboxymethyl)-N-(2-(bis(carboxymethyl) amino)ethyl)-(4-(N'-(2-aminoethyl) thiourea)phenyl) alanine trihydrochloride.

EXAMPLE 6

In this example, N-(carboxymethyl)-N-(2-aminoethyl)-N'-(carboxymethyl)-N'-(2'-(bis(carboxymethyl)amino)ethyl)-(4-aminophenyl)alanine (NH2-Compound B), a para-aminophenyl substituted bifunctional chelating agent presenting three amine and five carboxymethyl metal reacting groups according to the invention, was synthesized by reduction and subsequent acid hydrolysis of the material obtained on carboxymethylation of the product formed by reductive amination of 4-nitrophenylpyruvic acid with $N^4$-(N,N-diethylcarboxamidomethyl)diethylenetriamine.

In order to produce $N^4$-(N,N-diethylcarboxamidomethyl)diethylenetriamine, the doubly-protected triamine, $N^1,N^7$-bis(t-butoxycarbonyl)diethylenetriamine, was first prepared by adding over 30 minutes a solution of 26.0 grams of 2-(t-butoxycarbonyloxyimino)-2-phenyl-acetonitrile (105.6 mmol, Aldrich Chemical Co., Milwaukee, Wiss.) in 500 ml of THF to a stirred solution containing 5.44 grams of diethylenetriamine (52.7 mmol, Aldrich) and 15.97 grams of triethylamine (157.8 mmol) in 100 ml of THF cooled in an ice bath. After stirring for 2 more hours in the ice bath and then for a further 1 hour at room temperature, the THF was removed by evaporation under vacuum to give a green oil. This was dissolved in 200 ml of ethyl acetate and the resulting solution washed with 1000 ml of cold aqueous NaOH solution 5% (w/v). The organic layer was dried over anhydrous sodium sulfate then evaporated to dryness under vacuum. The resulting residue was purified by preparative HPLC using a Waters Delta Prep 3000 system (Millipore Corp., Milford, Mass.) equipped with a Prep-Pak 500 silica column and eluted with methanol:(2.5:97.5) methylene chloride. Fractions containing the desired product were identified by thin layer chromatography on silica plates (Whatman) developed in the same solvent system. These fractions were combined and evaporated to dryness under vacuum to yield 11.3 grams (71%) of $N^1,N^7$-bis(t-butoxycarbonyl) diethylenetriamine as a white solid.

In the next step, a diethylacetamide group was substituted at the central, unprotected nitrogen of the diethylenetriamine framework by refluxing together for 48 hours a mixture of 10.40 grams of $N^1,N^7$-bis(t-butoxycarbonyl)diethylenetriamine (34.29 mmol), 5.13 grams of 2-chloro-N,N-diethylacetamide (34.29 mmol, Aldrich) and 3.54 grams of triethylamine (34.98 mmol) in 200 ml of ethanol. After cooling to room temperature, the solvent was evaporated under vacuum and 200 ml of ethyl acetate added to the residue. The resulting mixture was filtered and the filtrate was washed with 1000 ml of 5% aqueous sodium carbonate solution. The organic layer was dried over anhydrous sodium sulfate then evaporated to dryness under vacuum, yielding a yellow oil. This was purified by preparative HPLC, using the Prep-Pak 500 silica column and eluting with (5:95) methanol:methylene chloride, fractions containing the desired product again being identified by thin layer chromatography on silica plates developed in the same solvent mixture used to elute the column. These were combined and evaporated to dryness to give 10.70 grams (75%) of $N^1,N^7$-bis(t-butoxycarbonyl)-$N^4$-(N,N-diethylcarboxamidomethyl)diethylenetriamine as a yellow oil. A 10.0 gram aliquot of this material (24.0 mmol) was de-protected by stirring in 75 ml of trifluoroacetic acid for 2 hours at room temperature. The reaction mixture was then evaporated to dryness, the residue dissolved in 100 ml of 4 M HCl and again evaporated to dryness under vacuum to yield 7.45 grams (95%) of $N^4$-(N,N-diethylcarboxamidomethyl)-diethylenetriamine trihydrochloride as a white solid.

The subsequent reductive amination step was achieved by adding a solution comprising 5.0 grams of the purified $N^4$-N,N-diethylcarboxamidomethyl)-diethylenetriamine trihydrochloride (15.35 mmol) in 15 ml of water to a solution comprising 3.14 grams of 4-nitrophenylpyruvic acid (15.01 mmol, prepared as described in example 1) in 50 ml of methanol. The pH of the resulting mixture was then brought to 6.0 using 7 M sodium hydroxide and 1.45 grams of sodium cyanoborohydride (23.07 mmol) was added. The pH of the mixture was readjusted to 6.0 using 6 M HCl then stirring was continued for a further 3 days at room temperature before 15 ml of concentrated HCl was added. Evaporation to dryness under vacuum gave an orange residue, which was suspended in 200 ml of water and washed with 1200 ml of ethyl acetate. Evaporation of the aqueous layer to dryness gave a yellow-white residue which was purified by preparative HPLC on the Prep-Pak 500 silica column eluting with (20:80) methanol:0.01 M triethylammonium acetate. Fractions containing the desired product were identified by thin layer chromatography on silica plates developed in (20:80) ammonium hydroxide:95% ethanol. These fractions were combined and the buffer salts were removed by re-applying this material to the preparative HPLC column, and eluting with (25:75) methanol:water. Fractions containing the desired product were again identified by thin layer chromatography, combined and evaporated to dryness. The resulting residue was dissolved in 50 ml of 4 M HCl and evaporated to dryness under vacuum to yield 1.96 grams of N-(2-aminoethyl)-N'-(N''-,N''-diethylcarboxamidomethyl)-N'-(2'-aminoethyl)-(4-nitrophenyl) alanine trihydrochloride as a white solid (25%).

A 1.0 gram aliquot of the purified N-(2-aminoethyl)-N'-(N'',N''-diethylcarboxamidomethyl)-N'-(2'-aminoethyl)-(4-nitrophenyl)alanine trihydrochloride (1.93 mmol) was then added to a solution comprising 1.16 grams of bromoacetic acid (8.33 mmol) in 20 ml of water and the mixture was heated to 45° C. The pH of the reaction mixture was brought to 12 by adding 7 M NaOH and the mixture was stirred at 45° C. for 24 hours while the pH was maintained at 12 by periodic addition of 7 M NaOH. The mixture was then cooled to room temperature and the pH adjusted to 1 using concentrated HCl. The mixture was washed with 150 ml of ethyl acetate then the pH of the aqueous layer was brought to 12 by adding 7 M NaOH. The resulting solution was applied to a Bio-Rad AGl-X4 column (formate form) which was eluted first with 500 ml of water then with 750 ml of 1.2 M formic acid. Ractions containing the desired product were identified by thin layer chromatography on silica plates developed in (20:80) ammonium hydroxide:95% ethanol. These fractions were combined and evaporated to dryness to give a yellow oil, which was redissolved in 50 ml of 4 M HCl. Evaporation to dryness of this solution yielded 0.60 grams (45% of N-(carboxymethyl)-N-(2-aminoethyl)-N'-(N',N''-diethylcarboxamidomethyl)-N'-(2'-(bis(carboxymethyl)amino)ethyl)-(4-nitrophenyl)alanine trihydrochloride in the form of a white solid.

In the next step, a solution comprising 1.1 grams of N-(carboxymethyl)-N-(2-aminoethyl)-N'-(N'',N''-diethylcarboxamidomethyl)-N'-(2'-(bis(carboxymethyl) amino)ethyl)-(4-nitrophenyl)alanine trihydrochloride (1.59 mmol), 300 ml of water and 30 ml of formic acid was hydrogenated at room temperature and 35 psi for 2 hours in the presence of 0.11 grams of 10% palladium on carbon as catalyst. The mixture was then filtered through celite to remove the catalyst and the filtrate was evaporated to dryness. The resulting residue was then dissolved in 100 ml of 4 M HCl and evaporated to dryness under vacuum to yield 1.1 grams (98%) of N-(carboxymethyl)-N-(2-aminoethyl)-N'-(N'',N''-diethyl-carboxamidomethyl)-N'-(2'-(bis(carboxymethyl) amino) ethyl)-(4-aminophenyl)alanine tetrahydrochloride.

A solution comprising 1.0 grams of N-(carboxymethyl)-N-(2-aminoethyl)-N'-(N'',N''-diethyl-carboxamidomethyl)-N'-(2'-(bis(carboxymethyl)amino)ethyl)-(4-amino-phenyl)alanine tetrahydrochloride (1.43 mmol) in 100 ml of 6 M HCl was refluxed for 60 hours. After cooling the reaction mixture to room temperature, the solvent was removed by evaporation under vacuum and the resulting residue was chromatographed on a Bio-Rad AG1-X4 column (formate form) eluted successively with 400 ml each of water, 0.1 M formic acid, 0.2 M formic acid and 0.3 M formic acid. The desired product eluted in 0.3 M formic acid, the relevant fractions being identified by thin layer chromatography on silica plates developed in (20:80) ammonium hydroxide:95% ethanol. These fractions were combined and evaporated to dryness. The resulting residue was dissolved in 50 ml of 4 M HCl and evaporated to dryness under vacuum to yield 0.2 grams (21%) of N-(carboxymethyl)-N-(2-aminoethyl)-N'-(carboxymethyl)-N'(2 '-(bis(carboxymethyl)amino)ethyl)-(4-aminophenyl)alanine tetrahydrochloride in the form of a white solid.

EXAMPLE 7

In this example, the 4-aminophenyl chelating agent of example 6 was converted to the corresponding 4-isothiocyanatophenyl chelating agent. A solution comprising 0.10 grams of N-(carboxymethyl)-N-(2-amino-ethyl)-N'-(carboxymethyl)-N'-(2'-(bis(carboxymethyl)amino)ethyl)-(4-aminophenyl)alanine tetrahydrochloride (0.16 mmol), 4 ml of 3 M HCl and 0.2 ml of 85% thiophosgene/carbon tetrachloride (v/v) (2.23 mmol) was stirred at room temperature for 6 hours. An additional 5 ml of carbon tetrachloride was then added and the aqueous and organic phases were separated. The aqueous layer was evaporated to dryness under vacuum to yield 0.093 grams (92%) of N-(carboxymethyl)-N-(2-aminoethyl)-4-isothiocyanatophenyl) alanine trihydrochloride.

EXAMPLE 8

In this example, N-(carboxymethyl)-N-(trans-(2-(bis(-carboxymethyl)amino)cyclohexyl))-(4-nitrophenyl) -alanine, a para-nitrophenyl substituted bifunctional chelating agent presenting two amine and four carboxymethyl metal reacting groups with the amine nitrogen atoms linked through a hydrocarbyl ring according to the invention, was synthesized by reduction and subsequent carboxymethylation of the imine obtained by the Schiff base condensation of 4-nitrophenylpyruvic acid with trans-1,2-diaminocyclohexane.

In the first step, 2.96 grams of trans-1,2-diaminocyclohexane (25.9 mmol, Aldrich) were added at room temperature to a solution comprising 5.0 grams of 4-nitrophenylpyruvic acid (23.9 mmol, prepared as in example 1) dissolved in 100 ml of methanol. The mixture was stirred at room temperature for 22 hours, then the resulting precipitate was filtered off, washed with methanol and dried under vacuum to yield 6.78 grams of 2-(trans-(2-aminocyclohexyl)imido)-3-(4-nitrophenyl) propionic acid.

In the next step, a solution comprising 0.24 grams of sodium borohydride (6.29 mmol) in 4 ml of ethanol was added to a suspension comprising 1.83 grams of 2-(trans-(2-aminocyclohexyl)imido)-3-(4-nitrophenyl)-propionic acid (6.0 mmol) and 0.2 grams of sodium hydroxide in 35 ml of ethanol in an ice bath. The reaction mixture was stirred in the ice bath for 30 minutes then at room temperature for a further 30 minutes. The pH of the reaction mixture was then brought to 6 by the addition of formic acid, causing a precipitate to form. This was filtered off and washed with ethanol. The filtrate plus washings were then evaporated to dryness under vacuum and the resulting residue was dissolved in water and brought to pH 10. This solution was washed with 50% ethyl acetate:50% diethyl ether, then the aqueous phase was chromatographed on a Bio-Rad AG1-X4 column (formate form) eluted first with 200 ml of water and subsequently with 500 ml of 0.05 M formic acid. Ultraviolet light absorbing and ninhydrin-positive fractions were combined and evaporated to dryness under vacuum. Trituration of the resulting residue with methanol gave a white solid which on drying under vacuum provided 0.91 grams of N-(trans-(2-aminocyclo-hexyl))-(4-nitrophenyl)alanine.

A 0.3 gram aliquot of the purified N-(trans-(2-aminocyclohexyl))-(4-nitrophenyl)alanine (0.99 mmol) dissolved in 20 ml of water were then added to a solution comprising 0.87 grams of bromoacetic acid (6.29 mmol) in 4 ml of water. The pH of the reaction mixture was adjusted to 13 by the addition of 0.2 grams of sodium hydroxide then 0.04 grams of sodium iodide were added and the resulting mixture was heated to 57° C. and stirred for 22 hours. After cooling to room temperature, the pH of the reaction mixture was restored to 13 by the addition of 5% aqueous sodium hydroxide. This solution was then chromatographed on a Bio-Rad AG1-X4 column (formate form) eluted successively with 75 ml of water, 100 ml of 0.2 M formic acid, 500 ml of 1.0 M formic acid and 250 ml of 5.0 M formic acid. The desired product eluted in the 5 M formic acid, ultra-violet light absorbing fractions being combined and evaporated to dryness to yield 0.02 grams of N-(carboxymethyl)-N-(trans-(2-(bis(carboxymethyl)amino)cyclohexyl))-(4-nitrophenyl)alanine.

EXAMPLE 9

In this example, the 4-isothiocyanatophenyl chelating agent (NCS-Compound A) produced according to example 3 was linked to an anti-CEA monoclonal antibody and the resulting conjugate compared with those obtained by a prior art procedure whereby a diethylenetriamine tetraacetate (DTTA) residue is introduced into a protein molecule by reaction of that protein with the bicyclic anhydride of DTPA, as disclosed by Hnatowich, et al., J. Immunol. Meth., 65, 147 (1983). The antibody was an immunoglobulin of the IgG$_1$ sub-type which binds to CEA with an affinity constant in excess of $10^9$ L.mol$^{-1}$ and does not react with non-specific cross-reacting antigen 1 (NCA-1). The antibody was produced in BALB/c mice and was isolated from ascites by affinity chromatography on protein A sepharose CL-4B (Sigma Chemical Co., St. Louis, Mo). After exhaustive dialysis against 0.1 M KH$_2$PO$_4$/0.15 M NaCl/0.05 M HEPES, pH 7.2, the antibody concentration was adjusted to 1.0 mg/ml and the solution stored at 2°-8° C. until needed. Antibody concentrations were determined by the Bradford dye-binding assay (Bio-Rad Laboratories, Richmond, Calif.), which was performed according to the manufacturer's directions. All buffers were prepared using water from a MILLI-Q system (Millipore Cowporation, Bedford, Mass.) purified to a resistivity of 18 megohm or greater. Antibody solutions were concentrated where necessary by ultrafiltration, using an ultrafiltration cell equipped with a membrane having a nominal molecular weight cut-off of 10,000 daltons (Amicon Corporation, Danvers, Mass.).

The antibody was conjugated to the 4-isothiocyanatophenyl chelating agent of example 3 according to the general procedure described by Meares, et al., Anal Biochem., 142, 68 (1984) the disclosure of which is hereby incorporated by reference. Specifically, 10 milligrams of the monoclonal antibody were buffer-exchanged by dialysis overnight at from about 2° to about 8° C. against 0.1 M $KH_2PO_4$/0.1 M $NaHCO_3$ (pH 8.5). After adjusting the antibody solution to a concentration of 1.0 mg/ml. N-(carboxymethyl)-N-(2-(bis(carboxymethyl) amino)ethyl)-(4-isothiocyanatophenyl) alanine dihydrochloride was added such as to give a 500-fold molar excess of chelator relative to antibody. The chelator/antibody solution was then incubated for 3 hours at 37° C. and the resulting conjugate (hereafter "anti-CEA-NCS-Compound A") dialysed for 48 hours at from about 2° to about 8° C. against 0.05 M sodium citrate (pH 6.0). The conjugate solution was then stored at −20° C. until needed.

The average chelator substitution in terms of moles of chelator per mole of antibody in the antibody-chelator conjugate was determined by the radiocobalt binding assay of Meares, et al., Anal. Biochem., 142, 68 (1984). The results of this procedure showed that the anti-CEA NCS-Compound A conjugate contained an average 2 of 4 chelators per antibody.

The formation of antibody-chelator inter-molecular aggregates was measured by SDS-polyacrylamide gel electrophoresis on 10% slab gels according to the methods of Laemmli, et al., Nature, 227 680 (1970). Gels were stained with Coomassie Blue and examined for the presence of bands other than those characteristic of light and heavy immunoglobulin chains. The presence of cross-linked material was indicated by the presence of a band which barely migrated into the gel and was well separated from the two bands arising from monomeric antibody-chelator conjugates, as described by Paik, et al., J. Nucl. Med., 24 1158 (1983). This procedure revealed no cross-linking in the anti-CEA-NCS-Compound A conjugate.

In order to compare the bifunctional Compound A conjugate of the present invention with chelate immunoconjugates of the same anti-CEA monoclonal antibody prepared by the prior art method, two DTTA conjugates were prepared: the first having a comparable level of substitution in terms of moles of chelator per mole of antibody, the second having a comparable low level of cross-linking. According to this procedure, the antibody was buffer-exchanged by dialysis overnight against a solution comprising 0.1 M $NaHCO_3$/0.05 M HEPES (pH 8.2). The antibody concentration was then adjusted to 1.0 mg/ml and the resulting solution was cooled to 0°-5° C. and stirred while a saturated solution of the bicyclic anhydride of DTPA (Sigma Chemical Co., St. Louis, Mo.) in DMSO was added drop-wise to the antibody solution. The pH of the reaction mixture was closely monitored throughout the addition process and was maintained at 8.2 by addition of 0.05 M NaOH. After mixing was complete, the solution was stirred at 0°-5° C. for an additional 15 minutes along with continued addition of base to maintain the pH at 8.2. The resulting conjugate was then dialysed for 2 days at from about 2° to about 8° C. against multiple changes of 0.05 M sodium citrate (pH 6.0) and then stored at −20° C. until needed. When this reaction was run with a 600:1 molar excess of bicyclic DTPA anhydride to antibody, the resulting conjugate contained an average of 5 chelators per antibody molecule (hereafter "anti-CEA-DTTA(5.0)"), and thus was comparable in its level of substitution to the anti-CEA-NCS-Compound A conjugate. However, the gel electrophoresis procedure detected virtually no monomeric immunoglobulin in the anti-CEA-DTTA(5.0) conjugate. When the coupling reaction was run using a 100:1 molar excess of bicyclic DTPA anhydride to antibody, a conjugate was obtained which was shown by electrophoresis to contain only small amounts of cross-linked material, the average substitution by radiocobalt binding assay being found to be 0.5 chelators per antibody (hereafter "anti-CEA-DTTA(0.5)").

EXAMPLE 10

In this example, the conjugates according to example 9 were evaluated using an enzyme linked immunosorbent assay (ELISA) procedure to determine the degree of immunoreactivity retained by the conjugated form compared with the free form. Ninety-six well microtiter plates (Immulon ™, Dynatech Laboratories, Inc., Arlington, Va.) were coated with purified CEA by incubating in each well 0.1 ml of a solution comprising 1.0 ug of the antigen in 10 mmol Tris (pH 7.4). After incubation overnight at room temperature, the wells were emptied and washed twice with deionized water. The wells were then overcoated by incubating for 2 hours at room temperature with a solution of bovine serum albumin (Sigma Chemical Co., St Louis, Mo.), 0.1% w/v in 0.1 M phosphate buffered normal saline (pH 7.4). The overcoated plates were stored until use at 2°-8° C. with a 0.1 ml aliquot of the overcoating solution in each well. Immediately prior to use, the plate was emptied and the wells were washed five times with deionized water.

Tandem ELISA assays were then performed on each antibody-chelator conjugate and on the native (underivatized) antibody from which the conjugate had been prepared. Both assays were run on the same microtiter plate, employing successive 2-fold dilutions of solutions adjusted to an initial protein concentration of 2.5 g/ml. Duplicate wells were run at each concentration for each antibody preparation.

According to the assay procedure, a solution of bovine serum albumin (1.0% w/v) and Tween (Sigma, 0.1%, by volume) in 0.05 ml of 0.1 M phosphate buffered normal saline (pH 7.4) was added to each well followed by 0.05 ml of the antibody preparation. The plate was then covered and incubated at 37° C. for 1 hour and then emptied and washed five times with deionized water. A 0.1 ml aliquot of solution comprising 0.06 ug/ml goat anti-mouse antibody conjugated to horseradish peroxidase (Kirkegaard & Perry Labs, Inc., Gaithersburg, Md.) 1.0% bovine serum albumin, 0.1% Tween and 0.1 M phosphate buffered normal saline (pH 7.4) was then added to each well. The plate was then covered and incubated at 37° C. for 1 hour. After being emptied and washed five times with deionized water, a 0.1 ml aliquot of orthophenylenediamine solution prepared according to the manufacturer's directions from a pre-formulated kit (Abbott Laboratories, North Chicago, Ill.) was added to each well. The plate was then incubated in the dark at room temperature for 15 minutes and 0.1 ml of 2 M $H_2SO_4$ was then added to each well to quench the enzymatic reaction. The color generated in each well was read at 490 nm using a microtiter plate reader (Minireader II, Dynatech).

Antibody titration curves were then prepared by plotting the mean optical density of duplicates at 490 nm against antibody concentration and the curve for the conjugate compared to that for the underivatized antibody. A semi-quantitative estimate of the immunoreactivity retained after labelling could be obtained by expressing the absorbance of the conjugate as a percentage of absorbance of the native antibody at 50% titration.

The results of the ELISA assays shown in FIGS. 1a, 1b and 1c show that the anti-CEA-DTTA(0.5) conjugate retains good immunoreactivity compared with the unconjugated antibody. On the other hand, the anti-CEA-DTTA(5.0) conjugate retains little activity as compared with the unconjugated antibody. The ELISA plot indicated that the anti-CEA-NCS-Compound A conjugate with an average of 4.0 chelators per antibody molecule maintained a significant level of immunoreactivity, close to that of the underivatized antibody. As the degree of substitution is increased, anti-CEA-NCS-Compound A conjugates fail to display any significant loss of immunoreactivity until a level of approximately 10 chelators per antibody is reached. Beyond this point, there appears a progressive loss of ability to bind CEA.

EXAMPLE 11

In this example, the 4-isothiocyanatophenyl chelating agent (NCS-Compound B) of example 7 was conjugated to the same anti-CEA monoclonal antibody employed in example 9. This was achieved by dialysis of 10 milligrams of the antibody against 0.1 M $KH_2PO_4$/0.1 M $NaHCO_3$ (pH 8.5) overnight at from about 2° to about 8° C. The antibody concentration was adjusted to 10 mg/ml then solid N-(carboxymethyl)-N-(2-aminoethyl)-N'-(carboxymethyl)-N'-(2'-(bis(carboxymethyl)amino)ethyl)-(4-isothiocyanatophenyl)alanine trihydrochloride was added such as to provide a 25-fold molar excess of chelating agent relative to the immunoglobulin. Gentle mixing caused the solid chelating agent to dissolve and produced a clear homogeneous solution which was incubated at 37° C. for 3 hours. The resulting conjugate solution was dialysed for 24 hours at from about 2° to about 8° C. against 0.05 M sodium citrate/0.01 M DTPA (pH 6.0) then for a further 24 hours at from about 2° to about 8° C. against 0.05 M sodium citrate (pH 6.0). Analysis of this anti-CEA monoclonal monoclonal antibody conjugate (hereafter "anti-CEA-NCS-Compound B") by the methods described in examples 9 and 10 revealed no inter-molecular aggregation, an average substitution of 13 chelators per antibody and complete retention of immunoreactivity.

EXAMPLE 12

In this example, the anti-CEA monoclonal antibody of examples 9, 10 and 11 was cleaved to provide the corresponding F(ab')$_2$ fragment, which was then conjugated to the 4-isothiocyanatophenyl (NCS-Compound A) chelating agent of example 3. Digestion of the antibody was carried out according to the general procedure described in Parham et al., J. Immunology, 131, 2895 (1983). Specifically, 10 milligrams of the antibody at a concentration of 2 mg/ml in phosphate buffered saline, pH 7.2, were added to 1.66 ml of 1.0 M citric acid, pH 3.5. To this solution was then added 0.83 ml of a solution of pepsin (0.25 mg/ml) in phosphate buffered:saline:citric acid (9:1 v/v), pH 3.7, followed by a further 1.66 ml of phosphate buffered saline, pH 7.2. The resulting mixture was incubated at 37° C. for 16 hours then the pepsin was inactivated by the addition of 1.66 ml of 1.0 M Tris. The solution was passed over a protein A-sepharose column (Pharmacia, N.J.) to remove intact immunoglobulin and $F_c$ fragments, then the eluate was chromatographed on a Bio-Gel P-100 column (Bio-Rad) to separate the immunoglobulin fragments from the pepsin. The desired F(ab')$_2$ fragments eluted in the void volume from this column.

In the next step, the F(ab')$_2$ fragments derived from the anti-CEA monoclonal antibody were dialysed overnight at from about 2° to about 8° C. against 0.1 M $KH_2PO_4$/0.1 M $NaHCO_3$ (pH 8.5). The concentration of the fragments was adjusted to 1.33 mg/ml, then solid N-(carboxymethyl)-N-(2-(bis(carboxymethyl)amino)ethyl)-(4-isothiocyanatophenyl)alanine dihydrochloride was added to a total of 2.0 mg of fragments such as to provide a final 250-fold molar excess of chelating agent to antibody fragment. After the solid chelating agent had dissolved, the resulting solution was incubated for 3 hours at 37° C. then dialysed for 24 hours at from about 2° to about 8° C. against 0.05 M sodium citrate/0.01 M EDTA (pH 6.0) then for a further 24 hours at the same temperature against 0.05 M sodium citrate, pH 6.0. Analysis of the resulting conjugate (hereafter "anti-CEA-F(ab')$_2$-NCS-Compound A") by the methods described in example 9 showed an average substitution of 1 chelator per F(ab')$_2$ fragment and no aggregated material by electrophoresis. The immunoreactivity of the fragment and its chelated conjugate were assessed by a minor modification of the procedure described in example 10, wherein the goat anti-mouse antibody conjugated to horseradish peroxidase used for color development in example 10 was replaced with a horseradish peroxidase conjugate of a goat antibody specific for the light chains of mouse immunoglobulin (Cooper Biomedical, Malvern, Pa.). When assayed in this manner, the immuno-reactivity of the chelate conjugate was identical to that of the underivatized fragment.

EXAMPLE 13

In this example, the monoclonal antibody B72.3 which recognizes a tumor-associated glycoprotein (TAG-72) and has been extensively described by Schlom et al., Int. J. Cancer, 29, 539 (1982), was conjugated to the 4-isothiocyanatophenyl chelating agent of example 3. The antibody was first dialysed overnight at from about 2° to about 8° C. against 0.1 M $KH_2PO_4$/0.1 M $NaHCO_3$ (pH 8.5) at an antibody concentration of 10 mg/ml. A 10 mg aliquot of the resulting antibody solution was then mixed with 1 milligram of N-(carboxymethyl)-N-(2-(bis(carboxymethyl) amino)ethyl)-(4-isothiocyanatophenyl)alanine trihydrochloride dissolved in 62 microliters of the same phosphate/bicarbonate buffer. The resulting molar ratio of chelator:antibody was 20:1. After incubation at 37° C. for 3 hours, the conjugate was dialysed for 24 hours at from about 2° to about 8° C. against 0.05 M sodium citrate/0.01 M EDTA (pH 6.0) then for a further 24 hours against 0.05 M sodium citrate, pH 6.0. Analysis of the resulting immunoconjugate by the methods described in example 9 revealed an average substitution of 1 chelator per antibody and a complete absence of cross-linked material. The immunoreactivity of B72.3 conjugates was determined by a minor modification of the ELISA procedure described in example 10, wherein the micro-titer plate was coated not with CEA but with bovine submaxillary mucin (a readily available antigen which cross-reacts with B72.3, Cooper Biomedical), the coating solution containing 10 micrograms of mucin in 10 mmol TRIS, pH 7.4. Otherwise, the procedure given in example 10 was followed exactly, except that washing steps employed 0.1 M $KH_2PO_4$/0.15 M NaCl, pH 7.4, in place of deionized water. When assayed in this fashion, the immunoreactivity of the chelate conjugate B72.3 (hereafter "B72.3-NCS-Compound A") was found to be approximately 50% that of the underivatized antibody.

EXAMPLE 14

In this example, the 4-(2-aminoethylthiourea)-phenyl chelating agent of example 5 (aminoethyl NCS-Compound A) was conjugated to the non-proteinaceous substrate poly(glutamic acid). 2.3 milligrams of the sodium salt of poly(glutamic acid) (0.16 mmol, Sigma Chemical Co., St. Louis, Mo.) containing an average of 90 glutamate residues per molecule and having an average molecular weight of 14,000 daltons was dissolved in 0.3 ml of dry dimethylformamide. 1.5 milligrams of 4-methylmorpholine (14.8 mmol) was added and the solution was cooled in an ice bath. To this stirred solution was added 2.0 milligrams of isobutylchloroformate (14.8 mmol) and the mixture was stirred in the ice bath for 1 hour. A further 4.5 milligrams of 4-methylmorpholine (44.4 mmol) were then added, followed by 10.0 milligrams of N-(carboxymethyl)-N-(2-(bis(carboxymethyl)amino) ethyl)-(4-(N'-(2-aminoethyl)thiourea)-phenyl)alanine trihydrochloride (14.8 mmol) and the resulting mixture was stirred overnight at room temperature. After diluting the reaction mixture to a total volume of 5.0 ml using 0.1 M $NaH_2PO_4$, pH 7.0, it was dialysed exhaustively against the same buffer, using dialysis tubing having a nominal molecular weight cutoff of 2,000 daltons (Spectrum Medical Industries, Inc., Los Angeles, lCA), then against deionized water. The resulting solution was lyophilized to yield a conjugate containing between 20 and 30 chelate residues per poly(glutamicacid) chain.

EXAMPLE 15

In this example, anti-CEA immunoconjugates were labelled with gamma-emitting indium[111] and their biodistributions were studied in nude mice bearing xenografts of human colorectal carcinoma line LS174T expressing high levels of CEA. The antibody-chelator conjugates included the anti-CEA-DTTA(0.5) conjugate, the anti-CEA-DTTA(5.0) conjugate and the anti-CEA-NCS-Compound A conjugate according to example 9. Each was labelled with indium[111] according to the procedure wherein a 0.1 ml aliquot of the antibody-chelator conjugate at a concentration of 1.0 mg/ml in 0.05 M sodium citrate (pH 6.0) was transferred to a plastic micro test tube and the pH was adjusted to 4.5-5.0 by addition of 6 M HCl. Six $\mu$l of carrier-free [111]$InCl_3$ in 0.04 M HCl 3(ca. 50–400 mCi/ml, typically about 80 mCi/ml, NEN-DuPont) was added to the conjugate solution and the pH was readjusted to 7.0 by addition of 6 M NaOH. After incubating the solution for 30 minutes at room temperature, unbound indium[111] was separated from antibody bound radioactivity by the centrifuged gel filtration column method described by Meares, et al., Anal. Biochem., 142, 68 (1984). The radiolabelled conjugate, which eluted from a Sephadex G-50 microcolumn on centrifugation for 2minutes at 100 g, was diluted into normal saline to a final concentration of 10 ug/ml. ELISA assays performed as described in example 10 showed no loss of immunoreactivity during the indium[111] labelling procedure.

Prior to injection into animals a 20 ul aliquot of this solution was incubated for 20 minutes at room temperature with 10 ul of a 0.1 M EDTA solution. The specificity of labelling was then assessed by thin layer chromatography according to the method of Meares, et al., which was carried out under the same conditions as in the radiocobalt binding assay. In all cases, greater than 90% of the indium[111] activity remained bound to the antibody in the face of the EDTA challenge. Specific activities of 2-3 mCi $^{111}$In/mg of protein were typically achieved.

Female athymic nude mice (nu/nu, BALB/C background, Charles River Biotechnology Services, Inc., Wilmington, Mass.) were prepared for biodistribution studies by subcutaneous injection in the right rear flank with a suspension of LS174T human colorectal carcinoma cells ($1.25 \times 10^6$–$2.5 \times 10^6$ cells in 0.1 ml normal saline). Within 1-2 weeks, solid tumors developed and reached a size of 0.4-0.8 grams.

Animals were then randomized into treatment groups, typically 5 mice per group, and injected intraveneously via the tail vein with 1.0 ug of one of the three radiolabelled antibody-conjugates in 0.1 ml normal saline. At various times after injection, animals were sacrificed by cervical dislocation and all their internal organs were removed, weighed and counted in a gamma counter (AUTO-LOGIC® gamma counter, Abbott Laboratories). Weighed aliquots of blood, muscle and skin were also counted, as was the residual carcass. The tail was counted separately to check for extravasation at the injection site and, when radioiodinated antibodies were used in control studies, the head was counted separately to evaluate thyroid uptake. A 0.1 ml aliquot of the injectate was counted at the same time as the tissues and the radioactivity measured in each tissue was then expressed as a percentage of this injected dose per gra of tissue.

Control studies were conducted involving implantation of a CEA antigen-negative tumor on the left rear flank of animals bearing an antigen positive tumor on their right flank. The MIA ATCC No. CRL 1420 human pancreatic carcinoma line was used for this purpose because it does not express appreciable amounts of CEA. The uptake of the anti-CEA antibody into the LS174T xenografts was some 8 to 10-fold greater than that of the MIA carcinoma.

Other control studies were conducted with anti-alpha-fetoprotein IgG, monoclonal antibodies labelled with iodine[125]. The labellings were conducted using the chloramine-T method to specific activities of 5 to 10 mCi/mg. These studies showed that uptake of non-CEA specific antibodies was an order of magnitude less than that of the anti-CEA antibodies. The injected doses of protein and the dissection and counting procedures in these studies were identical to those described above for the indium labelled reagents. Because time-course studies of anti-CEA antibody uptake into the LS174-tumor showed that tumor/blood ratios reached a maximum 2 days after intravenous injection of antibody, that was the interval chosen for studies with the chelator conjugates.

The results of the biodistribution studies are presented in tables 1 and 2. In table 1, the anti-CEA-NCS-Compound A conjugate of example 3 is compared with the prior art anti-CEA-DTTA(5.0) conjugate. The lower immunoreactivity and extensive cross-linking present inthe anti-CEA-DTTA(5.0) conjugate is correlated with a lower tumor uptake and elevated liver accumulation. The mean tumor/liver ratio in animals given the anti-CEA-5-NCS-Compound A conjugate according to the invention was 2.50±1.24. This was significantly higher ($p < 0.05$ according to a two-tailed Student's t test) than the anti-CEA-DTTA(5.0) conjugate which gave a means tumor/liver ratio of 0.92±0.28.

TABLE 1

| Organ | % of Injected Dose per Gram of Tissue | |
|---|---|---|
| | anti-CEA-NCS-Compound A | anti-CEA-DTTA (5.0) |
| Tumor | 21.6 (3.2) | 13.6 (3.8) |
| Blood | 10.3 (1.6) | 7.8 (2.5) |
| Liver | 10.3 (5.3) | 15.6 (4.5) |
| Spleen | 4.1 (0.8) | 5.6 (2.1) |
| Lungs | 5.5 (0.9) | 5.8 (2.2) |
| Heart | 4.7 (1.5) | 3.5 (0.5) |
| Gut | 1.5 (0.5) | 1.8 (0.3) |
| Kidney | 5.9 (0.8) | 7.0 (1.3) |
| Muscle | 1.5 (0.2) | 1.2 (0.4) |
| Skin | 3.8 (0.5) | 3.7 (0.7) |

All values are shown as mean (± SD) for n = 5.

TABLE 2

| Organ | % of Injected Dose per Gram of Tissue | |
|---|---|---|
| | anti CEA-NCS-Compound A | anti-CEA-DTTA (5.0) |
| Tumor | 21.6 (3.2) | 28.3 (4.9) |
| Blood | 10.3 (1.6) | 10.4 (2.7) |
| Liver | 10.3 (5.3) | 11.1 (1.2) |
| Spleen | 4.1 (0.8) | 7.1 (1.2) |
| Lungs | 5.5 (0.9) | 6.2 (1.2) |
| Heart | 4.7 (1.5) | 4.2 (0.7) |
| Gut | 1.5 (0.5) | 2.2 (0.7) |
| Kidney | 5.9 (0.8) | 11.7 (1.2) |
| Muscle | 1.5 (0.2) | 1.7 (0.4) |
| Skin | 3.8 (0.5) | 6.1 (0.7) |

All values are shown as mean (± SD) for n = 5.

In table 2, the anti-CEA-NCS-Compound A conjugate of example 9 was compared with the anti-CEA-DTTA(0.5) conjugate. Even though there was an 8-fold difference in the level of substitution, the conjugates were compared at equivalent levels of immunoreactivity. There was no significant difference in mean tumor/liver uptake ratios (2.56±0.43 for the anti-CEA-DTTA(0.5) conjugate versus 2.50±1.24 for the conjugate of the invention although absolute tumor uptake was significantly higher for the anti-CEA-DTTA (0.5) conjugate. At the same time, however, uptake into most other body organs was higher for the anti-CEA-DTTA(0.5) conjugate as reflected in the whole body retention of radioactivity at 48 hours which was significantly higher ($p < 0.001$) for the anti-CEA-DTTA(0.5) conjugate than for the conjugate of the invention. As a consequence, the absolute amount of radioactivity in the tumor expressed as a percentage of whole body radioactivity, which is an important index for radioimmunotherapy modeling, was not significantly greater for the anti-CEA-DTTA(0.5) conjugate than for the anti-CEA-NCS-Compound A conjugate of the invention.

TABLE 3

| | (Indium$^{111}$-anti-CEA Conjugates) | | |
|---|---|---|---|
| Indium$^{111}$ Conjugate | Tumor Wt. (Grams) | Whole Body Activity (% of Injected Dose) | Tumor Activity (% Whole Body Activity) |
| DTTA (0.5) | 0.53 (0.28) | 76 (6) | 21.5 (3.4) |
| DTTA (5.0) | 0.61 (0.43) | 66 (5) | 11.2 (5.0) |
| NCS-Cmpd A | 0.40 (0.21) | 54 (5) | 19.1 (4.7) |

All values shown are mean (± SD) for n = 5.

Table 3 shows the tumor uptake of indium$^{111}$ labelled anti-CEA conjugates in relation to whole body retention of activity in nude mice bearing LS174T tumors. Tumor uptake and whole body activity were measured at sacrifice 48 hours after intravenous injection of the conjugates into the nude mice. Tumor weights of the animals at sacrifice averaged approximately equal and were within a fairly narrow range. This is significant because large LS174T tumors tend to become necrotic with consequent low uptake while subcutaneous LS174T xenografts less than about 100 mg in weight are frequently poorly vascularized also with consequent low uptake rates. Consequently, tumor size can effect tumor uptake values even when these have been normalized to a unit weight basis.

EXAMPLE 16

In this example, the biodistribution of the anti-DEA-NCS-Compound B conjugate of example 11 was studied using an indium$^{111}$ radiolabel and the nude mouse xenograft model described in example 15. Th anit-NCS-Compound B conjugate of example 11 was labelled with indium$^{111}$ by the procedure described in example 15 and injected into mice bearing LS174T xenografts at a dose of 1.0 micrograms of conjugate per mouse. Biodistribution data, obtained at 48 hours post-injection as described in example 15, is shown in table 4.

TABLE 4

| Organ | % of Injected Dose per Gram of Tissue |
|---|---|
| Tumor | 19.7 (5.3) |
| Blood | 6.1 (1.9) |
| Liver | 3.9 (0.8) |
| Spleen | 4.3 (0.7) |
| Lungs | 3.7 (0.7) |
| Heart | 4.1 (1.4) |
| Gut | 1.0 (0.3) |
| Kidney | 3.3 (0.7) |
| Muscle | 2.0 (0.4) |
| Skin | 2.5 (0.8) |

All values are shown as mean (± SD) for n = 5.

When the biodistribution data for the anti-CEA-NCS-Compound B conjugate are compared with those for the conjugates of example 15, it is evident that while the tumor uptake of anti-CEA-NCS-Compound B is no greater than that seen with anti-CEA-NCS-Compound A and anti-CEA-DTTA(0.5), both the liver uptake and blood levels of radioactivity at 48 hours are strikingly lower with anti-CEA-NCS-Compound B. As a result, the tumor/liver uptake ratio for animals treated with anti-CEA-NCS-Compound B (5.3±1.7) is significantly higher than that for animals given either the anti-CEA-NCS-Compound A conjugate of this invention (2.5±1.2, $p < 0.01$) or the prior art anti-CEA-DTTA(0.5) conjugate (2.6±0.4, p 0.001). Similarily, the tumor/blood uptake ratio for anti-CEA-NCS-Compound B (3.40±1.15) is significantly higher than that for anti-CEA-NCS-Compound A (2.15±0.49, p<0.05).

TABLE 5

| Tumor Wt. (Grams) | Whole Body Activity (% of Injected Dose) | Tumor Activity (% Whole Body Activity) |
|---|---|---|
| 0.93 (0.41) | 59 (6) | 29.8 (13.6) |

All values are mean (± SD) for n = 5.

Table 5 shows the tumor uptake of indium[111] labelled anti-CEA-NCS-Compound B in relation to whole body retention of activity in nude mice bearing LS174T tumors at 48 hours post-injection. Although comparison of the data in table 5 with those in table 3 of example 15 suggests that the absolute amount of radioactivity in the tumor expressed as a percentage of whole body radioactivity is higher for the anti-CEA-NCS-Compound B conjugate than for the conjugates of example 15, this difference is not statistically significant and probably reflects the greater mean tumor weight in the animal given anti-CEA-NCS-Compound B.

EXAMPLE 17

In this example, the biodistribution of the anti-CEA-F(ab')$_2$-NCS-Compound A of example 12 was xenograft using an indium[111] radiolabel and the nude mouse xenograft model described in example 15. The conjugate was labelled with indium[111] by the procedure described in example 15 and injected into mice bearing LS174T xenografts at a dose of 1.0 microgram per mouse. Tables 6 and 7 present biodistribution data obtained 48 hours post-injection as described in example 15.

TABLE 6

| Organ | % of Injected Dose per Gram of Tissue |
|---|---|
| Tumor | 4.71 (1.01) |
| Blood | 0.33 (0.08) |
| Liver | 1.01 (0.06) |
| Spleen | 1.03 (0.21) |
| Lungs | 0.98 (0.04) |
| Heart | 1.01 (0.14) |
| Gut | 0.41 (0.10) |
| Kidney | 5.63 (1.41) |
| Muscle | 0.80 (0.15) |
| Skin | 0.67 (0.14) |

All values are mean (± SD) for n = 5.

TABLE 7

| Tumor Wt. (Grams) | Whole Body Activity (% of Injected Dose) | Tumor Activity (% Whole Body Activity) |
|---|---|---|
| 0.36 (0.26) | 14.1 (1.7) | 10.7 (4.9) |

All values are means (± SD) for n = 5.

Other than the high kidney uptake, reflecting accelerated renal clearance, the most prominent difference between the biodistribution of the antibody fragment and that of the corresponding conjugate of the intact antibody (example 15) is, as anticipated, the much lower level of radioactivity remaining in the blood at 48 hours. This results in a tumor/blood ratio (14.5±3.3) which greatly exceeds those seen with any of the intact antibody-conjugates of examples 15 and 16. This ability to achieve a high level of tumor contrast relative to the blood background and thus to image a tumor at early time periods post-injection is a major advantage offered by antibody fragments. A potential disadvantage when attempting therapy with cytotoxic radiometals is that the absolute uptake of radioactivity into the tumor is substantially lower than that seen with conjugates of the intact antibody. This remains true even when the tumor activity is expressed as a percentage of the whole body radioactivity at 48 hours, despite the latter being some 4-fold lower than the whole body retention of activity in animals given conjugates of the intact antibody.

EXAMPLE 18

In this example, the B72.3-NCS-Compound A conjugate of example 13 was labelled with indium[111] and a time course study was conducted in nude mice bearing a TAG-72 positive tumor on one flank (LS174T, see Keenan et al., J. Nucl. Med., 25, 1197 (1984)) and a TAG-72 negative xenograft on the opposing flank (the melanoma line, A375, was used for this purpose). This model has been described in detail by Colcher et al., Cancer Res., 44, 5744 (1984) and by Brechbiel et al., Inorg. Chem., 25, 2772 (1986). The method used to label the B72.3-NCS-Compound A conjugate with indium111 and the biodistribution procedures were as described in example 15. Each animal received 1.0 microgram of the conjugate via tail vein injection at time zero, then groups of mice were sacrificed serially at 24, 72, 120 and 168 hours post-injection. The data appear in table 8.

TABLE 8

| Tissue | 24 hrs. | 72 hrs. | 120 hrs. | 168 hrs. |
|---|---|---|---|---|
| LS174T | 16.3 (5.4) | 16.0 (3.4) | 13.2 (2.2) | 12.1 (2.7) |
| A375 | 3.8 (2.5) | 9.9 (3.5) | 9.0 (3.1) | 9.0 (2.1) |
| Blood | 16.0 (8.2) | 6.1 (0.8) | 4.2 (0.8) | 3.1 (0.9) |
| Liver | 4.2 (0.8) | 4.5 (0.6) | 5.7 (1.3) | 4.4 (1.0) |
| Spleen | 3.2 (0.8) | 4.0 (0.4) | 4.6 (1.2) | 4.7 (2.1) |
| Kidney | 3.3 (0.8) | 4.4 (1.1) | 5.3 (1.1) | 5.5 (1.4) |

All values are mean ± SD for n = 5.

Tumor uptake was maximal at 24 hours and slowly declined thereafter. Blood levels of radioactivity declined more precipitously, with the result that tumor/blood ratios increased progressively throughout the geriod of the study. Liver, spleen and kidney uptakes were modest at 24 hours and did not increase significantly at the later time points. Uptake into all other tissues was unremarkable.

EXAMPLE 19

In this example, a para-nitrophenyl substituted bifunctional derivative of the chelating agent ethylene glycol bis(2-aminoethyl ether)-N,N,N',N'-tetraacetic acid (EGTA) was prepared by the reductive alkylation of 1,8-diamino-3,6-dioxaoctane with p-nitrophenylpyruvic acid followed by carboxymethylation of the resulting product.

To a solution containing 0.21 grams of 4-nitrophenylpyruvic acid (1.0 mmol) in 5 ml of methanol was added a solution of 0.15 grams of 1,8-diamino-3,6-dioxaoctane (1.01 mmol) in 1 ml of water. The resulting deep red solution was treated with 4M hydrochloric acid until the pH reached 6.0. Then 0.1 grams of sodium cyanoborohydride was added. The resulting reaction mixture was stirred at room temperature at pH 6.0 for 4 days, then was acidified to a pH of 1.0 by the addition of concentrated hydrochloric acid. The resulting mixture was evaporated to dryness under vacuum and the residue dissolved in 100 ml of water. This aqueous solution was extracted with three 100 ml aliquots of ethyl acetate. Next, the aqueous phase was concentrated under vacuum, frozen in a isopropanol/dry ice bath and lyophilized. The lyophilized solid was dissolved in 5 ml of water and the pH of this solution was adjusted to 3.0 by addition of 4M hydrochloric acid. The solution was then applied to a Dowex 50X2-200 cation exchange column (bed size 25 grams) which was eluted successively with water, 1M hydrochloric acid, 2M hydrochloric acid and 4M hydrochloric acid. The desired product eluted in the 4M hydrochloric acid fractions. These fractions were combined, concentrated under vacuum and subjected to four cycles of dilution with 50 ml of water and reconcentration under vacuum, to remove excess hydrochloric acid. The residue after complete removal of solvents under vacuum was redissolved in water, frozen in an isopropanol/dry ice bath and lyophilized to afford 0.075 grams of the desired product, N-(1-amino-3,6-dioxaoctyl)-4-nitrophenylalanine.

0.06 grams of the above intermediate, N-(1-amino-3,6-dioxaoctyl)-4-nitrophenylalanine (0.145 mmol), was dissolved in a solution of 0.44 ml of 1M sodium hydroxide and 0.05 ml of DMF. This solution was then added dropwise to a stirred solution of 0.06 grams of bromoacetic acid (0.43 mmol) in 0.44 ml of 1M sodium hydroxide solution. Then an additional 0.44 ml of 1M sodium hydroxide was added to the solution. The resulting reaction mixture was stirred at about 80° C. for 2.5 hours, and then was cooled to room temperature and acidified to pH 1 by the addition of concentrated hydrochloric acid. The solution was concentrated under vacuum and the residue was subjected to four cycles of redissolution in 100 ml of water and re-evaporation under vacuum, to remove excess hydrochloric acid. The resulting oily residue was dissolved in 10 ml of water, frozen in an isopropanol/dry ice bath and lyophilized. This gave 0.19 grams of a light beige colored powder which was dissolved in a minimum volume of water and the pH adjusted to 8 using sodium hydroxide. The resulting solution was applied to a Bio-Rad AGl-X4 anion exchange column (formate form, bed size 5 grams) which was successively eluted with water, 1M formic acid, 2M formic acid, 3M formic acid and 5M formic acid. The product eluted in the 1M formic acid fractions. The fractions were combined, concentrated to dryness under vacuum and lyophilized to yield 0.04 grams of the desired product, N-(1-carboxy-2-(p-nitrophenyl)-ethyl)-1,8-diamino-3,6-dioxaoctane-N,N',N'-triacetic acid.

EXAMPLE 20

In this example, a conjugate was formed between cholic acid, which is a bile acid containing a side chain bearing an aliphatic carboxylic acid group and the 4-(2-aminoethylthiourea)phenyl bifunctional derivative of ethylenediaminetetraacetic acid described in Example 5. The conjugate was obtained by first forming an active ester derivative of cholic acid and then reacting this with the aliphatic amine substituent in the bifunctional chelator.

The active ester was prepared by dissolving 1.1 grams of cholic acid (2.4 mmol) and 0.35 grams of N-hydroxysuccinimide (3.04 mmol) in a mixture of 20 ml of THF and 5 ml of acetonitrile and cooling the resulting solution in an ice bath. A solution of 0.47 grams of 1-ethyl-3-(3-dimethylaminopropyl)carbodiimide hydrochloride (2.4 mmol) in 5 ml of THF was then added dropwise, followed by 0.34 grams of triethylamine (2.4 mmol). The reaction mixture was stirred at room temperature for 17 hours. The solvents were then removed by evaporation under vacuum. The resulting residue was dissolved in 150 ml of chloroform and then extracted successively with four 100 ml aliquots of cold water, four 100 ml aliquots of cold 1M hydrochloric acid, three 100 ml aliquots of cold saturated sodium bicarbonate solution. The organic phase was then separated and dried over anhydrous sodium sulfate. The dessicant was filtered off and the filtrate evaporated to dryness under vacuum to yield 1.18 grams of the desired compound in the form of a white solid.

A solution of 31 milligrams of N-(carboxymethyl)-N-(2-(bis(carboxymethyl)amino)ethyl)-(4-(N'-(2-aminoethyl) thiourea)phenyl)alanine trihydrochloride (0.05 mmol, prepared as described in Example 5) and 36 milligrams of triethylamine (0.36 mmol) in 1 ml of THF was stirred at room temperature as a solution of 25.5 milligrams of the cholic acid active ester (0.05 mmol) in 0.25 ml of DMF was added dropwise. This reaction was stirred at room temperature for six days in a tightly stoppered flask. The solvents were then removed by evaporation under vacuum and the residue was dissolved in 5 ml of water. The pH of this solution was adjusted to about 8 using 1M sodium hydroxide, then it was was applied to a Bio-Rad AGl-X4 anion exchange colume (formate form, bed size 7 grams). The column was eluted successively with water, 1M formic acid, 3M formic acid, 4M formic acid, 4.5M formic acid, 5M formic acid and 1M hydrochloric acid. The desired material eluted in the 5M formic acid fractions. These fractions were combined and evaporated to dryness under vacuum. The resulting residue was subjected to four cycles of redissolution in 100 ml of 4M hydrochloric acid and re-evaporation to dryness. The residue from this process was dissolved in 150 ml of water and lyophilized to give a sticky yellow solid. This was redissolved in 50 ml of water, frozen in an isopropanol/dry ice bath and again lyophilized to yield the desired cholic acid-EDTA conjugate in the form of a light beige powder, yielding 30 milligrams.

EXAMPLE 21

In this example, the cholic acid EDTA conjugate prepared in Example 20 was labelled with indium-111 and its biodistribution was determined in mice.

20 microliters of 1.0M sodium acetate buffer, pH 6, were placed in a micro test tube together with 20 microliters of indium-111 chloride solution (13.4 micro-Curies per microliter, Atomic Energy of Canada, Ltd.) and 40 microliters of a stock solution of the cholic acid-EDTA conjugate (prepared as in Example 20) obtained by dissolving 2 milligrams of the conjugate in 2 ml of 0.1M sodium acetate buffer, pH 6. The contents of the tube were mixed and allowed to stand at room temperature for 30 minutes. Forty microliters of the reaction mixture were then applied to a small column (bed volume 300 microliters) containing Chelex resin (Sigma Chemical Co., 50–100 mesh) and unbound indium was removed by centrifugation of the column, as described by Meares et al., Anal. Biochem., 142, 68 (1984). The column eluent was 0.1M sodium acetate, pH 6 (600 microliters). The indium-111 labeled cholic acid-EDTA conjugate was collected in the column eluate after centrifugation and found to have a specific activity of 8.6 microcuries per microliter.

Five BALB/c mice were anesthetized by an i.p. injection of nembutal and then were given i.v. injections via the tail vein of 100 microliters of the indium-111-EDTA-cholic acid conjugate. The mice were sacrificed by cervical dislocation at 2 hours post injection and the biodistribution of indium-111 activity was determined. These data appear in TABLE 9

TABLE 9

| Tissue | % of injected dose per Gram of tissue* |
|---|---|
| Blood | 0.99 |
| Liver | 1.01 |
| Heart | 0.39 |
| Kidney | 2.9 |
| G.I. Tract | 6.2 |
| Gall Bladder | 56.0 |
| Spleen | 0.40 |
| Lungs | 1.2 |
| Muscle | 0.26 |

*Values shown are means for n = 5.

These data indicate that a significant fraction of the injected dose was cleared through the liver with subsequent biliary excretion into the gut. Substantial activity was present in the gut at 2 hours with marked accumulation in the gall bladder. The residual activity seen in the kidneys probably indicates that that fraction of the injected activity which was not cleared by the liver was rapidly excreted into the urine.

EXAMPLE 22

In this example, the ability of the cholic acid-EDTA-indium-111 conjugate to function as an imaging agent for the hepatobiliary system was evaluated in a rabbit model.

The cholic acid-EDTA conjugate prepared in Example 20 was labeled with indium-111 as described in Example 21. The resulting preparation had a specific activity of 1.69 mCi/ml. A 1.0 mCi dose of this material (0.59 ml) was injected into the left marginal ear vein of a female New Zealand rabbit which had been fasted for two days prior to the study. Five minutes after receiving the injection, the rabbit was anesthetized with Innovar-Vet and a series of planar gamma camera images were obtained at 5 minute intervals over the following hour. Additional images were acquired at 80, 95, 110, 125 and 140 minutes post-injection. The rabbit was then allowed to regain conciousness. At 25 hours post-injection, the rabbit was again anesthetized and a further gamma camera image was obtained.

The resulting images showed rapid uptake of the radiolabel into the liver, such that the first image obtained at 10 minutes post-injection showed intense liver localization. Subsequently, the activity was rapidly cleared from the liver with focal accumulations of label becoming apparent in the lower abdomen at 20-25 minutes post-injection and no observable activity remaining in the liver at 1 hour. Activity also was apparent in the kidneys at the 10 minute time point, but this cleared rapidly such that there was no discernable kidney activity at 35 minutes post-injection. The urinary bladder showed intense activity at all early time points, but not in the 25 hour image at which time the animal had emptied its bladder. Activity in the 25 hour image was diffusely distributed throughout the G.I. tract.

The results of this study establish the utility of the cholic acid-EDTA-In-111 conjugate as a radiopharmaceutical for imaging of the hepatobiliary system. A substantial portion of this conjugate is rapidly extracted from circulation by the liver, from which it is then excreted through the bile duct into the gut, allowing the potential identification of physiological defects in these structures by Nuclear Medicine procedures.

From the above examples, it is obvious to those of skill in the art that the conjugates and methods of the invention are useful for imaging of localized concentrations of antigens by external photoscanning such as described in Goldenberg, et al. In such a method, the conjugate is introduced into a patient and the body of the patient is scanned for concentrations of the conjugate. It should also be apparent that the conjugates of the invention may be utilized in in vitro diagnostic methods such as immunoassays or nucleic acid hybridization assays. In diagnostic methods such as sandwich hybridization techniques, conjugates according to the invention comprising indicator means are useful in indicating the presence of analytes. Conjugates and methods of the invention are also useful in therapeutic methods wherein an antibody-metal ion conjugate in which the metal ion emits cytotoxic radiation is introduced into a patient such that cytotoxic radiation may be directed to tumors while minimizing the toxic effects to healthy tissues. Consequently, only such limitations should be placed on the invention as appear in the following claims.

We claim:

1. A substrate conjugate of the formula:

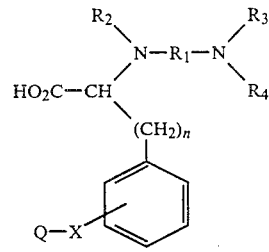

wherein Q is a substrate molecule and wherein X is meta or para and is a residue of a substrate reactive moiety;

wherein n=0 to about 10;

wherein $R_1$ is selected from the group consisting of:
—$(CH_2)_q$—,
—$[(CH_2)_qN(R_5)(CH_2)_r]$—,
—$[(CH_2)_qO(CH_2)_rO(CH_2)_s]$—,
—$[(CH_2)_qN(R_5)(CH_2)_rN(R_6)(CH_2)_s]$—,

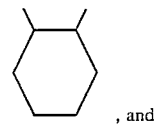, and

wherein q=2 or 3,
r=2 or 3, and
s=2 or 3;

wherein $R_2$, $R_3$, $R_4$, $R_5$ and $R_6$ are the same or different and are selected from the group consisting of:
hydrogen
$CH_2CO_2H$
ortho-$CH_2C_6H_4OH$, and wherein when $R_1=(CH_2)_q$
$R_2$ and $R_3$ may be fused to form a hydrocarbyl ring of the formula $$-(CH_2)_tN(R_7)(CH_2)_uN(R_8)(CH_2)_v-$$

wherein $t=2$ or 3,
$u=2$ or 3, and
$v=2$ or 3
wherein $R_7$ and $R_8$ are selected from the group consisting of:
hydrogen,
$-CH_2CO_2H$, and
ortho—$CH_2C_6H_4OH$.

2. The substrate conjugate according to claim 1 wherein X is the residue of a substrate reactive moiety selected from the group consisting of:

| | |
|---|---|
| $-NH_2$, | (AMINO) |
| $-NN^+$, | (DIAZONIUM) |
| $-NCS$, | (ISOTHIOCYANATE) |
| $-NCO$, | (ISOCYANATE) |
| $-NHNH_2$, | (HYDRAZINE) |
| $-NHCSNHNH_2$, | (THIOSEMICARBAZIDE) |
| $-NHCOCH_2Cl$, | (CHLOROACETAMIDE) |
| $-NHCOCH_2Br$, | (BROMOACETAMIDE) |
| $-NHCOCH_2I$, | (IODOACETAMIDE) |
| $-N_3$, | (AZIDE) |
| $-NHCONH(CH_2)_mNH_2$, | (AMINOALKYLUREA) |
| $-NHCSNH(CH_2)_mNH_2$, | (AMINOALKYLTHIOUREA) |
| $-NHCONHNH_2$, | (SEMICARBAZIDE) |

(MALEIMIDE)

(structure: N-maleimide)

(HALOTRIAZINE)

(structure: -NH-triazine with Y and Z substituents)

(META-(DIHYDROXYBORYL)PHENYLTHIOUREA)

(structure: -NHCSNH-phenyl-B(OH)2)

wherein Y is selected from the group consisting of Cl, Br and F;
wherein Z is selected from the group consisting of Cl, Br, F, OH and $OCH_3$;
wherein $m=1$ to about 10.

3. The substrate conjugate according to claim 1 wherein X is para and is the residue of a substrate reactive moiety selected from the group consisting of:
$-NH_2$,
$-NCS$,
$-NHCSNHNH_2$ and
$-NHCSNH(CH_2)_2NH_2$
wherein $n=1$,
wherein $R_1$ is selected from the group consisting of
$-(CH_2)_2-$,
$[(CH_2)_2O(CH_2)_2O(CH_2)_2]$
$-[(CH_2)_2N(CH_2CO_2)(CH_2)_2]-$ and (cyclohexyl structure)

wherein $R_2$, $R_3$ and $R_4$ are $-CH_2CO_2H$.

4. The substrate conjugate according to claim 1 wherein Q is selected from the group consisting of proteins, glycoproteins, peptides, poly(amino acids), lipids, carbohydrates, polysacchari.des, nucleosides, nucleotides, nucleic acids, bile acids, and intact cells.

5. The substrate comjugate according to claim 1 wherein Q is drugs.

6. The substrate conjugate according to claim 3 wherein Q is selected from the group consisting of proteins, glycoproteins, peptides, poly(amino acids), lipids, carbohydrates, polysaccharides, nucleosides, nucleotides, nucleic acids, bile acids, and intact cells.

7. The substrate conjugate according to claim 3 wherein Q is drugs.

8. The substrate conjugate according to claim 4 wherein Q is an antibody or an antibody fragment.

9. The substrate conjugate according to claim 4 wherein Q is cholic acid.

10. The substrate conjugate according to claim 3 wherein Q is an antibody or antibody fragment.

11. The substrate conjugate according to claim 3 wherein Q is cholic acid.

12. The substrate conjugate according to claim 8 wherein Q is a monoclonal antibody or its fragment.

13. The substrate conjugate according to claim 8 wherein Q is a recombinant derived antibody or antibody fragment.

14. The substrate conjugate according to claim 8 wherein the antibody or fragment is specifically reactive with a tumor associated antigen.

15. The substrate conjugate according to claim 14 wherein the tumor associated antigen is selected from the group consisting of carcinoembryonic antigen, mucins including TAG-72, human milk fat globule antigens, IL-2 receptors and transferrin receptors.

16. A substrate metal ion conjugate of the formula:

(structure with $R_2$, $R_3$, $R_4$, M, $R_1$, N, $HO_2C-CH$, $(CH_2)_n$, Q-X, phenyl ring)

wherein Q is a substrate molecule;
wherein M is a metal ion;
wherein X is meta or para and is a residue of a substrate reactive moiety;
wherein $n=0$ to about 10;

wherein $R_1$ is selected from the group consisting of:
—$(CH_2)_q$—,
—$[(CH_2)_qN(R_5)(CH_2)_r]$—,
—$[(CH_2)_qO(CH_2)_rO(CH_2)_s]$—,
—$[(CH_2)_qN(R_5)(CH_2)_rN(R_6)(CH_2)_s]$—,

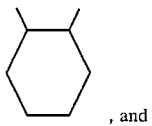, and

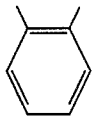

wherein q=2 or 3,
r=2 or 3, and
s=2 or 3;
wherein $R_2$, $R_3$, $R_4$, $R_5$ and $R_6$ are the same or different and are selected from the group consisting of:
hydrogen
$CH_2CO_2H$
ortho-$CH_2C_6H_4OH$, and
wherein when $R_1 = (CH_2)_q$
$R_2$ and $R_3$ may be fused to form a hydrocarbyl ring of the formula —$(CH_2)_tN(R_7)(CH_2)_uN(R_8)(CH_2)_v$— wherein t=2 or 3,
u=2 or 3, and
v=2 or 3
wherein $R_7$ and $R_8$ are selected from the group consisting of:
hydrogen,
—$CH_2CO_2H$, and
ortho-$CH_2C_6H_4OH$.

17. The substrate-metal ion conjugate according to claim 16 wherein X is para and is a residue of a substrate reactive moiety selected from the group consisting of:
—$NH_2$,
—NCS,
—$NHCSNHNH_2$ and
—$NHCSNH(CH_2)_2NH_2$
wherein n=1,
wherein $R_1$ is selected from the group consisting of
—$(CH_2)_2$,
—$[(CH_2)_2O(CH_2)_2O(CH_2)_2]$—,
—$[(CH_2)_2N(CH_2CO_2)(CH_2)_2]$— and

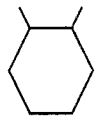

wherein $R_2$, $R_3$ and $R_4$ are —$CH_2CO_2H$.

18. The substrate-metal ion conjugate according to claim 16 wherein M is selected from the group consisting of gamma radiation emitters, beta radiation emitters, alpha radiation emitters, fluorescent metal ions and paramagnetic metal ions.

19. The substrate-metal ion conjugate according to claim 17 wherein M is selected from the group consisting of gamma radiation emitters, beta radiation emitters, alpha radiation emitters, fluorescent metal ions and paramagnetic metal ions and wherein Q is selected from the group consisting of proteins, glycoproteins, peptides, poly(amino acids), lipids, carbohydrates, polysaccharides, nucleosides, nucleotides, nucleic acids, bile acids, and intact cells.

20. The substrate-metal ion conjugate according to claim 17 wherein M is selected from the group consisting of gamma radiation emitters, beta radiation emitters, alpha radiation emitters, fluorescent metal ions and paramagnetic metal ions and wherein Q is drugs.

21. The substrate-metal ion conjugate according to claim 18 wherein M is selected from the group consisting of Indium, Gallium, Technetium, Lead, Scandium, Copper, Yttrium, Ruthenium, Palladium, Rhodium, Samarium, Rhenium, Bismuth, Terbium, Europium, Gadolinium, Iron, Barium, Gold, Platinum, Nickel, Tin, Aluminum, Mercury, Iridium, Osmium, Thorium and Uranium.

22. A substrate-metal ion conjugate according to claim 16 wherein X is the residue of a substrate reactive moiety selected from the group consisting of:

| | |
|---|---|
| —$NH_2$, | (AMINO) |
| —$NN^+$, | (DIAZONIUM) |
| —NCS, | (ISOTHIOCYANATE) |
| —NCO, | (ISOCYANATE) |
| —$NHNH_2$ | (HYDRAZINE) |
| —$NHCSNHNH_2$, | (THIOSEMICARBAZIDE) |
| —$NHCOCH_2Cl$, | (CHLOROACETAMIDE) |
| —$NHCOCH_2Br$, | (BROMOACETAMIDE) |
| —$NHCOCH_2I$, | (IODOACETAMIDE) |
| —$N_3$, | (AZIDE) |
| —$NHCONH(CH_2)_mNH_2$, | (AMINOALKYLUREA) |
| —$NHCSNH(CH_2)_mNH_2$, | (AMINOALKYLTHIOUREA) |
| —$NHCONHNH_2$, | (SEMICARBAZIDE) |
|  | (MALEIMIDE) |
| 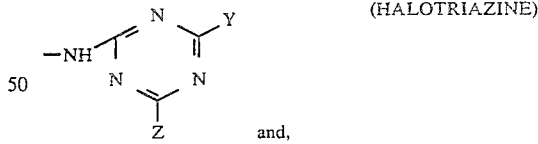 | (HALOTRIAZINE) |
| 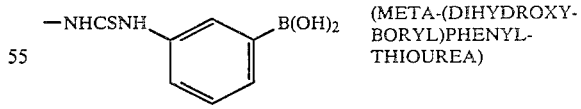 and, | (META-(DIHYDROXYBORYL)PHENYLTHIOUREA) | wherein Y is selected from the group consisting of Cl, Br and F;
wherein Z is selected from the group consisting of Cl, Br, F, OH and $OCH_3$;
wherein m=1 to about 10.

23. The substrate-metal ion conjugate according to claim 16 wherein Q is an antibody or antibody fragment.

24. The substrate-metal ion conjugate according to claim 16 wherein Q is cholic acid.

25. The substrate-metal ion conjugate according to claim 23 wherein M is indium.

26. An in vivo diagnostic method comprising introducing into a patient a solution comprising an antibody-metal ion conjugate according to claim 23 and scanning the body for concentrations of said conjugate.

27. An in vivo therapeutic method comprising introducing into a patient an antibody-metal ion conjugate according to claim 23 wherein said metal ion emits cytotoxic radiation.

28. An in vitro diagnostic method comprising introducing into a test medium an antibody-metal ion conjugate according to claim 23 and assaying for concentrations of said conjugate.

29. An in vivo diagnostic method comprising introducing into a patient a solution comprising a bile acid chelate-metal ion conjugate according to claim 19 and scanning the body for concentrations of said conjugate.

* * * * *